US009963517B2

(12) United States Patent
Sliwkowski et al.

(10) Patent No.: US 9,963,517 B2
(45) Date of Patent: May 8, 2018

(54) ISOFORM SPECIFIC ANTI-HER4 ANTIBODIES

(71) Applicants: Genentech, Inc., South San Francisco, CA (US); University of Turku, Turku (FI)

(72) Inventors: Mark X. Sliwkowski, San Carlos, CA (US); Klaus Elenius, Turku (FI); Maija Hollmen, Turku (FI)

(73) Assignees: Genentech, Inc., South San Francisco, CA (US); University of Turku, Turku (FI)

( * ) Notice: Subject to any disclaimer, the term of this patent is extended or adjusted under 35 U.S.C. 154(b) by 0 days. days.

(21) Appl. No.: 14/946,318

(22) Filed: Nov. 19, 2015

(65) Prior Publication Data

US 2016/0075798 A1 Mar. 17, 2016

Related U.S. Application Data

(62) Division of application No. 13/130,789, filed as application No. PCT/US2009/065712 on Nov. 24, 2009, now abandoned.

(60) Provisional application No. 61/117,903, filed on Nov. 25, 2008.

(51) Int. Cl.

| | |
|---|---|
| ***A61K 6/00*** | (2006.01) |
| ***A61K 39/00*** | (2006.01) |
| ***C07K 16/40*** | (2006.01) |
| ***C07K 16/32*** | (2006.01) |
| ***G01N 33/574*** | (2006.01) |

(52) U.S. Cl.

CPC .............. *C07K 16/40* (2013.01); *C07K 16/32* (2013.01); *G01N 33/57492* (2013.01); *A61K 2039/505* (2013.01); *C07K 2317/30* (2013.01); *C07K 2317/73* (2013.01); *C07K 2317/76* (2013.01); *C07K 2317/77* (2013.01); *C07K 2317/92* (2013.01); *G01N 2333/71* (2013.01)

(58) Field of Classification Search

None

See application file for complete search history.

(56) References Cited

U.S. PATENT DOCUMENTS

| | | | | |
|---|---|---|---|---|
| 5,811,098 | A * | 9/1998 | Plowman | A61K 47/48561 424/1.49 |
| 6,696,290 | B2 | 2/2004 | Fitzpatrick et al. | |
| 7,332,579 | B2 | 2/2008 | Gerritsen et al. | |
| 7,704,498 | B2 | 4/2010 | Gerritsen et al. | |
| 7,846,453 | B2 | 12/2010 | Godowski et al. | |
| 2011/0293614 | A1 | 12/2011 | Elenius et al. | |

FOREIGN PATENT DOCUMENTS

| | | | |
|---|---|---|---|
| EP | 599274 | | 6/1994 |
| WO | 1999/19488 | | 4/1999 |
| WO | WO 99/19488 | * | 4/1999 |

OTHER PUBLICATIONS

Gilmour et al. (Cancer Research 61: 2169-2176, Mar. 1, 2001).*
Agus et al., "argeting ligand-activated ErbB2 signaling inhibits breast and prostate tumor growth." Cancer Cell 2(2):127-137 ( 2002).
Elenius et al., "A novel juxtamembrane domain isoform of HER4_ErbB4: Isoform-specific Tissue Distribution and Differential Processing in Response to Phorbol Ester" Journal of Biol. Chemistry 272:26761-26768 ( 1997).
Gilmour et al., "Expression of erbB-4/HER-4 Growth Factor Receptor Isoforms in Ovarian Cancer." Cancer Research 61:2169-2176 ( 2001).
Haugen et al., "Expression of c-erbB-3 and c-erbB-4 Proteins in Papillary Thyroid Carcinomas." Cancer Research 56:1184-1188 ( 1996).
Hollmen et al., "Suppression of Breast Cancer Cell Growth by a Monoclonal Antibody Targeting Cleavable ErbB4 Isoforms." Oncogene 28:1309-1319 ( 2009).
Hurwitz et al., "Supression an a promotion of tumor growth by monoclonal antibodies to ErbB-2 differentially correlate with cellular uptake" Pro Natl Acad Sci 92(8):3353-3357 ( 1995).
Iivanainen et al., "Intra- and Extracellular Signaling by Endothelial Neuregulin-1." Experimental Cell Research 131:2896-2909 ( 2007).
Junttila et al., "Cleavable ErbB4 Isoform in Estrogen Receptor-Regulated Growth of Breast Cancer Cells." Cancer Research 65:1384-1396 ( 2005).
Junttila et al., "ErbB4 and its Isoforms; Selective Regulation of Growth Factor Responses" Trends Cardiovasc Med. 10(7):304-310 ( 2000).
Junttila et al., "Identification of Patients with Transitional Cell Carcinoma of the Bladder Overexpressing ErbB2, ErbB3, or Specific ErbB4 Isoforms: Real-Time Reverse Transcription—PCR Analysis in Estimation of ErbB Receptor Status from Cancer Patients" Clinical Cancer Research 9:5346-5357 ( 2003).
Kainulainen et al., "A Natural ErbB4 Isoform that does not Activate Phosphoinositide 3-kinase Mediates Proliferation but not Survival or Chemotaxis" Journal of Biological Chemistry 275:8641-8649 ( 2000).
Klapper et al., "Tumor-inhibitory Antibodies to HER-2_ErbB-2 May Act by Recruiting c-Cbl and Enhancing Ubiquitination of HER-2." Cancer Research 60:3384-3388 ( 2000).
Komuro et al., "WW Domain-containing Protein YAP Associates with ErbB-4 and Acts as a Co-transcriptional Activator for the Carboxyl-terminal Fragment of ErbB-4 That Translocates to the Nucleus" Journal of Biological Chemistry 278:33334-33341 ( 2003).
Lee et al., "Presenilin-dependent Secretase-like Intramembrane Cleavage of ErbB4." Journal of Biological Chemistry 277:6318-6323 ( 2002).
Liu et al., "Stimulated ErbB4 internalization is necessary for neuregulin signaling in neurons." Biochem. Biophys. Res. Commun. 354(2):505-510 ( 2007).

(Continued)

*Primary Examiner* — Alana Harris Dent

(57) ABSTRACT

Compositions and methods useful for detecting and treating cancers which express the HER4 JM-a isoform are disclosed.

3 Claims, 15 Drawing Sheets

(56) References Cited

OTHER PUBLICATIONS

Lodge et al., "Type 1 Growth Factor Receptor Expression in Node Positive Breast Cancer." Journal Clinical Pathol. 56(4):300-304 ( 2003).
Maatta et al., "Proteolytic Cleavage and Phosphorylation of a Tumor-associated ErbB4 Isoform Promote Ligand-independent Survival and Cancer Cell Growth" Molecular Biology of the Cell 17:67-79 ( 2006).
Muraoka-Cook et al., "The Intracellular Domain of ErbB4 Induces Differentiation of Mammary Epithelial Cells." Molecular Biology of the Cell 17:4118-4129 ( 2006).
Ni et al., "Secretase Cleavage and Nuclear Localization of ErbB-4 Receptor Tyrosine Kinase." Science 294(5549):2179-2181 ( 2001).
Paborsky et al., "Mammalian Cell Transient Expression of Tissue Factor for the Production of Antigen" Protein Eng 3(6):547-553 (May 1990).
Plowman et al., "Ligand-specific Activation of HER4/p180HER4, a Fourth Member of the Epidermal Growth Factor Receptor Family" Proc. Natl. Acad. Sci. USA 90:1746-1750 ( 1993).
Prewett et al., "Mouse-human Chimeric Anti-epidermal Growth Factor Receptor Antibody C225 Inhibits the Growth of Human Renal Cell Carcinoma Xenografts in Nude Mice." Clinical Cancer Research 4:2957-2966 ( 1998).
Prickett et al., "Analysis of the Tyrosine Kinome in Melanoma Reveals Recurrent Mutations in ERBB4." Nature Genetics 41(10):1127-1132 ( 2009).
Rio et al., "Tumor Necrosis Factor-alpha-converting Enzyme is Required for Cleavage of erbB4_HER4." Journal of Biological Chemistry 275(14):10379-10387 ( 2000).
Schlessinger et al., "Nuclear Signaling by Receptor Tyrosine Kinases; the First Robin of Spring." Cell 127(1):45-48 ( 2006).
Srinivasan et al., "Expression of the c_erbB/4/HER4 Protein and mRNA in Normal Human Fetal and Adult Tissues and in a Survey of Nine Solid Tumour Types." Journal of Pathology 185(3):236-245 ( 1998).
Srinivasan et al., "Expression of the c-erbB-3/HER-3 and c-erbB-4/HER-4 Growth Factor Receptors and Their Ligands, Neuregulin-1, Neuregulin-1, and Betacellulin, in Normal Endometrium and Endometrial Cancer." Clinical Cancer Research 5:2877-2883 ( 1999).
Srinivasan et al., "Nuclear Expression of the c-erbB-4/HER-4 Growth Factor Receptor in Invasive Breast Cancers." Cancer Research 60:1483-1487 ( 2000).
Stern et al., "ErbBs in Mammary Development." Experimental Cell Research 284:89-98 ( 2003).
Sunada et al., "Monoclonal Antibody Against Epidermal Growth Factor Receptor is Internalized." Proc. Natl. Acad. Sci. USA 83:3825-3829 ( 1986).
Sundvall et al., "Differential Nuclear Localization and Kinase Activity of Alternative ErbB4 Intracellular Domains." Oncogene 26:6905-6914 ( 2007).
Sundvall et al., "Role of ErbB4 in Breast Cancer." J. Mammary Gland Bio and Neo 13:259-268 ( 2008).
Suo et al., "EGFR Family Expression in Breast Carcinomas. c-erbB-2 and c-erbB-4 Receptors Have Different Effects on Survival." Journal of Pathology 196:17-25 ( 2002).
Tang et al., "Ribozyme-mediated Down-regulation of ErbB-4 in Estrogen Receptor-positive Breast Cancer Cells Inhibits Proliferation Both in Vitro and in Vivo" Cancer Research 59(20):5315-5322 ( 1999).
Vecchi et al., "Selective Cleavage of the Heregulin Receptor ErbB-4 by Protein Kinase C Activation." Journal of Biological Chemistry 271(31):18989-18995 ( 1996).
Yeh et al., "Cardiovascular Complications of Cancer Therapy." Journal of the American College of Cardiology 53(24):2231-2247 ( 2009).
Zhang et al., "Transformation of NIH 3T3 Cells by HER3 or HER4 Receptors Requires the Presence of HER1 or HER2." Journal of Biological Chemistry 271(7):3884-3890 ( 1996).
Zhu et al., "Coregulation of Estrogen Receptor by ErbB4_HER4 Establishes a Growth-Promoting Autocrine Signal in Breast Tummor Cells." Cancer Research 66:7991-7998 ( 2006).
Gullick, "c-erbB-4/HER4: friend or foe?" J Pathol 200:279-281 ( 2003).
Plowman et al., "Heregulin induces tyrosine phosphorylation of HER4/p180\\\superscript:erbB4\\\" Nature 366:473-475 (Dec. 2, 1993).
Witton et al., "Expression of the HER1-4 family of receptor tyrosine kinases in breast cancer" J Pathol 200(3):290-297 ( 2003).
Kim et al., "Chimeric receptor analyses of the interactions of the ectodomains of ErbB-1 with epidermal growth factor and of those of ErbB-4 with neuregulin" Eur J Biochem 269:2323-2329 ( 2002).
Gura (Science 278:1041-1042, 1997).
Bao et al., "Targeting ligand-activated ErbB2 signaling inhibits breast and prostate tumor growth." Journal of Cell Biology 161(6):1133-1141 ( 2003).
Barnes et al., "Absence of HER4 expression predicts recurrence of ductal carcinoma in situ of the breast." Clinical Cancer Research 11:2163-2168 ( 2005).
Baulida et al., "All ErbB receptors other than the epidermal growth factor receptor are endocytosis impaired." Journal of Biol. Chemistry 271:5251-5257 ( 1996).
Bieche et al., "Prognostic value of ERBB family mRNA expression in breast carcinomas." Int. Journal of Cancer 106:758-765 ( 2003).
Borrell-Pages et al., "TACE is required for the activation of the EGFR by TGF-alpha in tumors." EMBo Journal 22(5):1114-1124 ( 2003).
Carter, "Improving the efficacy of antibody-based cancer therapies." Nature Review Caner 1(2):118-129 ( 2001).
Cheng et al., "Ectodomain cleavage of ErbB-4; characterization of the cleavage site and m80 fragment." journal of Biol. Chemistry 278:38421-38427 ( 2003).
Cho et at, "Structure of the extracellular region of HER2 alone and in complex with the Herceptin Fab." Nature 421(6924):756-760 ( 2003).
Chu et al., "Cardiotoxicity associated with tyrosine kinase inhibitor sunitinib." Lancet 370:2011-2019 ( 2007).
Cuello et al., "Down-regulation of the erbB-2 receptor by trastuzumab (Herceptin) Enhances Tumor Necrosis Factor-related Apoptosis-inducing Ligand-mediated Apoptosis in Breast and Ovarian Cancer Cell Lines That Overexpress erbB-2" Cancer Research 61:4892-4900 ( 2001).
Ding et at, "Somatic Mutations Affect Key Pathways in Lung Adenocarcinoma." Nature 455:1069-1075 ( 2008).
Elenius et al., "Characterization of a Naturally Occurring ErbB4 Isoform That does not Bind or Activate Phosphatidy Inositol 3-Kinase" Oncogene 18:2607-2615 ( 1999).
Force et al., "Cardiotoxicity of the New Cancer Therapeutics—Mechanisms of, and Approaches to, the Problem." Drug Discovery Today 13(17-18):778-784 ( 2008).
Franklin et al., "Insights into ErbB Signaling from the Structure of the ErbB2-pertuzumab Complex." Cancer Cell 5(4):317-328 ( 2004).
Furger et al., "Granulosa Cell Tumors Express HER4 and are Sensitive to the Cytotoxic Action of Heregulin-B2/PE40." Cancer Research 58:1773-1778 ( 1998).
Gilbertson et al., "ERBB Receptor Signaling Promotes Ependymoma Cell Proliferation and Represents a Potential Novel Therapeutic Target for This Disease" Clinical Cancer Research. 8(10):3054-3064 ( 2002).
Gilbertson et al., "Prognostic Significance of HER2 and HER4 Coexpression in Childhood Medulloblastoma." Cancer Research 57:3272-3280 ( 1997).
Gilmore et al., "secErbB4-26/549 Antagonizes Ligand-induced HER4 tyrosine Phosphorylation" Oncology Research 14(11-12):589-602 ( 2004).
Gomes et al., "Membrane Targeting of Rab GTPases is Influenced by the Prenylation Motif" Molecular Biol. of the Cell 14:1882-1899 ( 2003).

* cited by examiner

| Mab | Isotype | Epitope | Specificity |
|---|---|---|---|
| 4-1440 | IgG2b, k | B | 4 |
| 4-1459 | IgG2a, k | D | 4 |
| 4-1460 | IgG1, k | C | 4 |
| 4-1461 | IgG2a, k | E | 4 |
| 4-1462 | IgG1, k | C | 4 |
| 4-1464 | IgG2b, k | C | 4 |
| 4-1465 | IgG2a, k | L | 3, 4 |
| 4-1472 | IgG2a, k | M | 4 |
| 4-1473 | IgG2a, k | F | 4 |
| 4-1474 | IgG2b, k | G | 4 |
| 4-1475 | IgG2b, k | P | 4 |
| 4-1476 | IgG2a, k | K | 4 |
| 4-1477 | IgG2a, k | Q | 4 |
| 4-1479 | IgG2a, k | D | 4 |
| 4-1481 | IgG2a, k | H | 3, 4 |
| 4-1482 | IgG2b, k | H | 4 |
| 4-1483 | IgG1, k | R | 3, 4 |
| 4-1484 | IgG1, k | E | 4 |
| 4-1485 | IgG2a, k | F | 4 |
| 4-1492 | IgG2b, k | A | 4 |
| 4-1494 | IgG2b, k | B | 4 |
| 4-1495 | IgG2b, k | A | 4 |
| 4-1496 | IgG1, k | A | 3, 4 |
| 4-1497 | IgG1, k | N | 4 |
| 4-1498 | IgG2b, k | E | 4 |
| 4-1535 | IgG2b, k | B | 4 |
| 4-1536 | IgG2b, k | A | 4 |
| 4-1537 | IgG2b, k | B | 4 |
| 4-1543 | IgG2a, k | O | 4 |

Figure 2

ISOFORM SPECIFIC ANTI-HER4 ANTIBODIES

RELATED APPLICATIONS

This application claims the benefit of priority under 35 USC 119(e) of U.S. Provisional Application No. 61/117,903, filed Nov. 25, 2008, the disclosure of which is incorporated herein by reference in its entirety.

FIELD OF THE INVENTION

The present invention is directed to antibodies useful for detecting and treating cancer and to methods of using those antibodies.

BACKGROUND OF THE INVENTION

ErbB/HER receptors form a subfamily of receptor tyrosine kinases that includes EGFR (also known as ErbB1 or HER1), HER2 (c-Neu, ErbB2), HER3 (ErbB3), and HER4 (ErbB4). ErbB receptors are selectively activated by a number of EGF-like growth factors leading to cellular responses, such as cell proliferation, differentiation, migration, or survival. ErbB receptors consist of a glycosylated extracellular domain, a single transmembrane domain, and an intracellular domain including a tyrosine kinase enzyme. Ligand binding to the receptor extracellular domain triggers receptor dimerization, subsequent activation of the kinase domain, receptor autophosphorylation, and multiple downstream signaling cascades (1).

EGFR and HER2 are well-established oncogenes and cancer drug targets. They are implicated in the pathogenesis of various epithelial and neural malignancies, and their overactivity is associated with poor patient outcome (2-4). Targeted therapeutics including both monoclonal antibodies and small molecular weight kinase inhibitors blocking the functions of these receptors have shown therapeutic effect on patient survival in clinical trials. Cetuximab (ERBITUX™, Imclone, Inc.) is a chimeric monoclonal antibody that blocks ligand binding to EGFR, leading to a decrease in receptor dimerization, autophosphorylation and activation of signaling pathways (5). Cetuximab is currently approved for clinical use in late-stage chemorefractory colorectal cancer and locally or regionally advanced squamous cell carcinoma of the head and neck. Trastuzumab (HERCEPTIN™, Genentech, Inc.) is a humanized monoclonal antibody against the extracellular domain of HER2 currently used for the treatment of ErbB2-overexpressing breast cancers in both adjuvant setting and for advanced disease (6-9).

HER4 receptor antagonists have been shown to be useful in controlling excessive migration and/or proliferation or smooth muscle cells and, in particular, for the treatment of stenosis. See U.S. Pat. No. 7,332,579.

The significance of HER4 in cancer is poorly understood. Some observations indicate that HER4 receptor is downregulated in various cancers, or that its expression is associated with favorable prognostic markers, such as estrogen receptor expression (10, 11). On the other hand, HER4 has been reported to have high expression levels in several cancers such as thyroid (12), ovarian (13), and breast cancer (14), as well as medulloblastoma (15), and ependymoma (16). Furthermore, the significance of HER4 expression levels for clinical outcome is conflicting (17). One of the plausible explanations for these contradictory data is that four structurally and functionally different isoforms are generated from a single HER4 gene by alternative splicing (18, 19). These isoforms have different tissue distribution profiles and differ in their ability to promote tumorigenesis in breast cancer cell lines (26).

Accordingly, it is desirable to provide a therapeutic that is directed to specific isoforms of the HER4 receptor to more precisely treat HER4 mediated disorders.

SUMMARY OF THE INVENTION

One aspect of the invention provides for an isolated anti-HER4 antibody that specifically binds to the HER4 JM-a isoform. In one embodiment, the antibody competes for binding to the JM-a isoform with the anti-HER4 antibody mAb 1479 produced by the hybridoma cell line deposited with ATCC having accession No. PTA-9655. In another embodiment, the antibody binds to the same epitope as the epitope to which the monoclonal antibody mAb 1479 produced by the hybridoma cell line deposited with the ATCC having accession No. PTA-9655 binds. In some embodiments, the antibody is a chimeric, human, or humanized antibody.

In another embodiment, the isolated anti-HER4 antibody that specifically binds to the HER4 JM-a isoform comprises a fragment from the monoclonal antibody mAb 1479 produced by the hybridoma cell line deposited with the ATCC having accession No. PTA-9655 that specifically binds to the HER4 JM-a isoform. In one embodiment, the fragment comprises the variable region of the monoclonal antibody mAb 1479. In some embodiments, the antibody is a humanized antibody. In some embodiments, the antibody is affinity matured. In one embodiment, the isolated anti-HER4 antibody comprises the monoclonal antibody mAb 1479 produced by the hybridoma cell line deposited with the ATCC having accession No. PTA-9655 or humanized form thereof.

In some embodiments, the isolated anti-HER4 antibody is linked to a cytotoxic agent.

In some embodiments, the isolated anti-HER4 antibody that specifically binds to the HER4 JM-a isoform has less cardiotoxicity than an anti-HER4 antibody that is not specific for the HER4 JM-a isoform.

Another aspect of the invention provides for a method of inhibiting the proliferation of a cancer cell that expresses the HER4 JM-a isoform, comprising contacting the cancer cell with an therapeutically effective amount of an anti-HER4 antibody that specifically binds to the HER4 JM-a isoform. In one embodiment, the anti-HER4 antibody reduces HER4 ectodomain shedding. In some embodiments, the cancer cell is a breast cancer, ovarian cancer, or medulloblastoma cell.

Another aspect of the invention provides for a method of treating cancer in a patient whose cancer expresses the HER4 JM-a isoform comprising administering to the patient a therapeutically effective amount of an anti-HER4 antibody that specifically binds to the HER4 JM-a isoform. In one embodiment, the anti-HER4 antibody reduces HER4 ectodomain shedding. In some embodiments, the cancer to be treated is breast cancer, ovarian cancer, or medulloblastoma.

Another aspect of the invention provides for a method of treating cancer in a patient by selecting a patient whose cancerous cells express the HER4 JM-a isoform and administering to the patient a therapeutically effective amount of an anti-HER4 antibody that specifically binds to the HER4 JM-a isoform. In one embodiment, the anti-HER4 antibody reduces HER4 ectodomain shedding. In some embodiments, the cancer to be treated is breast cancer, ovarian cancer, or medulloblastoma.

Another aspect of the invention provides for a method of treating cancer in a patient by selecting a patient whose cancerous cells comprise increased levels of shed Her4 ectodomain as compared with non-cancerous cells of the same tissue type and administering to the patient a therapeutically effective amount of an anti-HER4 antibody that specifically binds to the HER4 JM-a isoform. In one embodiment, the anti-HER4 antibody reduces HER4 ectodomain shedding. In some embodiments, the cancer to be treated is breast cancer, ovarian cancer, or medulloblastoma.

Another aspect of the invention provides for a method of reducing the risk of cardiotoxicity associated with cancer therapy in a patient with cancer comprising administering to the patient a therapeutically effective amount of an anti-HER4 antibody that specifically binds to the HER4 JM-a isoform. In one embodiment, the patient's cancer overexpresses the HER4 JM-a isoform. In one embodiment, the patient's cancer comprises increased levels of shed Her4 ectodomain as compared with non-cancerous cells of the same tissue type. In some embodiments, the patient's cancer is breast cancer, ovarian cancer, or medulloblastoma.

Another aspect of the invention provides for a method of detecting the presence of shed HER4 ectodomain in a sample of cells comprising contacting the cells with an antibody that specifically binds to the JM-a HER4 isoform.

Yet another aspect of the invention provides for a method of diagnosing a tumor in a patient comprising detecting the presence of shed HER4 ectodomain in the tumor. In one embodiment, the method of detecting comprises contacting an anti-HER4 antibody that specifically binds to the JM-a isoform of HER4 with a sample obtained from the tumor. In one embodiment, the method comprises comparing the level of shed HER4 ectodomain in the tumor to the level of shed HER4 ectodomain in a non-cancerous control sample.

BRIEF DESCRIPTION OF THE DRAWINGS

FIG. 2 is a table describing characteristics of certain HER4 monoclonal antibodies.

DETAILED DESCRIPTION

Definitions

Figure 1:
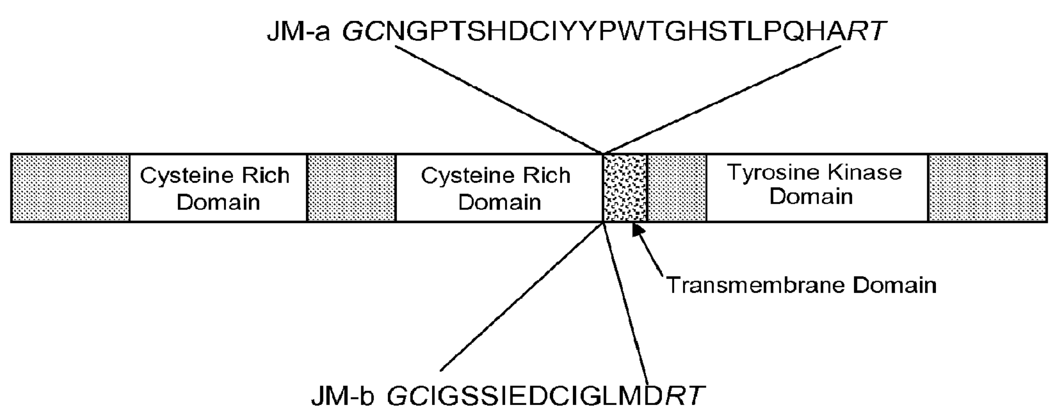
FIG. 1 is a diagram showing the alternative juxtamembrane domain HER4 isoforms JM-a (SEQ ID NO:1) and JM-b (SEQ ID NO:2).

Unless defined otherwise, technical and scientific terms used herein have the same meaning as commonly understood by one of ordinary skill in the art to which this invention belongs, and are consistent with: Singleton et al 1994 Dictionary of Microbiology and Molecular Biology, 2nd Ed., J. Wiley & Sons, New York, N.Y.; and Janeway et al 2001 Immunobiology: the immune system in health and disease 5th Ed., Garland Publishing, New York.

The term "HER4 polypeptide" or "HER4 receptor", as used herein, refers, unless specifically or contextually indicated otherwise, to any native or variant polypeptide that is produced from a HER4 gene disclosed, for example, in European Patent Application No. (EP) 599,274; Plowman at al., Proc. Natl. Acad. Sci. USA, 90:1746-1750 (1993); and Plowman et al., Nature, 366:473-475 (1993). In one embodiment, the HER4 gene is a human HER4 gene. The terms "HER4" and "ErbB4" are used interchangeably in the art. The term encompasses naturally occurring forms, naturally occurring variant forms (e.g., alternatively spliced forms), naturally occurring allelic variants, and may include naturally occurring post-translational modifications such as glycosylation and GPI modifications.

The term "wild type" generally refers to a polypeptide comprising the amino acid sequence of a naturally occurring HER4 protein.

A "native sequence polypeptide" comprises a polypeptide having the same amino acid sequence as the corresponding polypeptide derived from nature. Such native sequence polypeptides can be isolated from nature or can be produced by recombinant or synthetic means. The term "native sequence polypeptide" specifically encompasses naturally occurring truncated or secreted forms of the specific polypeptide (e.g., an extracellular domain sequence), naturally occurring variant forms (e.g., alternatively spliced forms), naturally occurring allelic variants of the polypeptide and may include naturally occurring post-translational modifications such as glycosylation etc.

The term "amino acid sequence variant" refers to naturally occurring polypeptide having an amino acid sequence that differs to some extent from the predominant native sequence polypeptide. The amino acid sequence variants possess substitutions, deletions, and/or insertions at certain positions within the amino acid sequence.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991, and which code is found in WO 2007/001851.

The "extracellular domain" or "ECD" refers to a form of the polypeptide that is essentially free of the transmembrane and cytoplasmic domains. It will be understood that any transmembrane domains identified for the polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al 2003 Jour. of Immunology 170:4854-4861). Antibodies may be murine, human, humanized, chimeric, or derived from other species. An antibody is a protein that is capable of recognizing and binding to a specific antigen (Janeway et al 2001 Immunobiology: the immune system in health and disease, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species such as human, murine, or rabbit. For the structure and properties of the different classes of antibodies, see Basic & Clinical Immunology, 8th edition, Stites and Terr (eds.), Mcgraw-Hill, Appleton & Lange, Norwalk, Conn., 1994 at Chapter 6.

"Native antibodies" are usually heterotetrameric glycoproteins of about 150,000 Daltons, composed of two identical light (L) chains (of which there are two types called kappa and lambda), and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

A "parent antibody" may comprise a native or wild type sequence. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (2) to a degree sufficient to obtain at least 15 residues of N-terminal or internal amino acid sequence by use of a spinning cup sequenator, or (3) to apparent homogeneity by SDS-PAGE under reducing or nonreducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

"Antibody fragments" comprise a portion of a full-length antibody, generally the antigen binding or variable region thereof. Examples of antibody fragments include Fab, Fab', $F(ab')_2$, and Fv fragments; diabodies; linear antibodies; minibodies (U.S. Pat. No. 5,641,870, Example 2; Zapata et al 1995 Protein Eng. 8(10): 1057-1062); Olafsen et al 2004 Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts and glycosylation differences. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. For example, the monoclonal antibodies to be used in accordance with the present invention may be made by the hybridoma method first described by Kohler et al 1975 Nature 256:495, or may be made by recombinant DNA methods (see for example: U.S. Pat. No. 4,816,567; U.S. Pat. No. 5,807,715). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding 1986 Monoclonal Antibodies: Principles and Practice, pp. 59-103 Academic Press). The antibodies may also be isolated from phage antibody libraries using the techniques described in Clackson et al 1991 Nature 352:624-628; Marks et al 1991 J. Mol. Biol. 222:581-597.

The DNA that encodes the antibody may be modified to produce "chimeric or fusion antibody polypeptides", for example, by substituting human heavy chain and light chain constant domain ($C_H$ and $C_L$) sequences for the homologous murine sequences (U.S. Pat. No. 4,816,567; and Morrison et al 1984 Proc. Natl. Acad. Sci. USA, 81:6851), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al 1984 Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all, or substantially all, of the FRs are those of a human immunoglobulin sequence. The humanized antibody optionally also will comprise at least a portion of an immunoglobulin constant region (Fe), typically that of a human immunoglobulin. The Fc fragment comprises the carboxyterminal portions of both H chains held together by disulfides. The effector functions of antibodies are determined by sequences in the Fc region, which region is also the part recognized by Fc receptors (FcR) found on certain types of cells (Jones et al 1986 Nature 321:522-525; Riechmann et al 1988 Nature 332:323-329; Presta 1992 Curr. Op. Struct. Biol. 2:593-596; Verhoeyen et al 1988 Science 239:1534-1536; Sims et al 1993 J. Immunol 151:2296; Chothia et al 1987 J. Mol. Biol. 196:901). Other methods use a particular framework region derived from the consensus sequence of all human antibodies of a particular subgroup of light or heavy chains (Carter et al 1992 Proc. Natl. Acad. Sci. USA, 89:4285; Presta et al 1993 J. Immunol. 151:2623).

A "human antibody" is one which possesses an amino acid sequence which corresponds to that of an antibody produced by a human and/or has been made using any of the techniques for making human antibodies as disclosed herein. Transgenic animals (e.g., mice) are available that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge (Jakobovits et al 1993 Proc. Natl. Acad. Sci. USA, 90:2551; Jakobovits et al 1993 Nature, 362:255-258; Bruggemarm et al 1993 Year in Immuno. 7:33; U.S. Pat. No. 5,545,806; U.S. Pat. No. 5,569,825; U.S. Pat. No. 5,591,669; U.S. Pat. No. 5,545,807; and WO 1997/17852.

A "cysteine-engineered" antibody is where one or more amino acids of any form of wild-type, murine parent monoclonal antibody, human or humanized antibody are replaced with a cysteine amino acid. The engineered cysteine amino acid is a free cysteine acid and not part of an intrachain or interchain disulfide unit. The DNA encoding one or more amino acid residues of the antibody of interest is modified or "engineered" such that one or more codons for a cysteine amino acid is introduced and thus free cysteine is available on the expressed antibody for further modification such a conjugation to a cytotoxic drug.

An "antigen" is a predetermined polypeptide, carbohydrate, nucleic acid, lipid, hapten or other naturally occurring or synthetic compound to which an antibody can selectively bind. The cell membrane of a cell can present a "cell surface exposed antigen".

An antibody "binds" a molecular target or an antigen of interest when the binding to that antigen is with sufficient affinity and specificity that an antibody-antigen complex is formed that is useful in targeting the epitopes of the antigen. The epitopes of the antigen may be exposed on the surface of cells or may be present on an isolated protein.

The term "specific binding" or "specifically binds to" or is "specific for" a particular molecular target or an antigen of interest or an epitope on a particular molecular target or an antigen of interest means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. In one embodiment, such terms refer to binding where a molecule binds to a particular polypeptide or epitope on a particular polypeptide without substantially binding to any other polypeptide or polypeptide epitope. Alternatively, such terms can be described by a molecule having a Kd for the target of at least about 10-4 M, 10-5 M, 10-6 M, 10-7 M, 10-8 M, 10-9 M, 10-10 M, 10-11 M, 10-12 M, or greater.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

An "antibody-antigen complex" or an "antibody-drug conjugate-antigen complex" is formed as a result of specific binding. For example, when the antibody is one that binds HER4 specifically, or an isoform of HER4 specifically, it will usually preferentially bind one or more epitopes found on the native HER4, or isoform thereof, and may be an antibody that does not have significant binding affinity (e.g. non-specific binding affinity or cross-reactivity), with other antigens or proteins or other isoforms of HER4. In such embodiments, the extent of non-specific binding affinity or cross-reactive binding to non-HER4, or other isoforms of HER4, will be less than 10%, 5%, 2%, or 1% as determined by fluorescence activated cell sorting (FACS) analysis or radioimmunoprecipitation (RIA).

An "intact antibody" herein is one comprising $V_L$ and $V_H$ domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al 1991 Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region", "HVR", or "HV", when used herein refers to the regions of an antibody variable domain that are hypervariable in sequence and/or form structurally defined loops. Generally, antibodies comprise six hypervariable regions; three in the $V_H$ (H1, H2, H3), and three in the $V_L$ (L1, L2, L3). A number of hypervariable region delineations are in use and are encompassed herein. The Kabat Complementarity Determining Regions (CDRs) are based on sequence variability and are the most commonly used (Kabat et al 1991). Chothia refers instead to the location of the structural loops (Chothia and Lesk 1987 J. Mol. Biol. 196:901-917). The "contact" hypervariable regions are based on an analysis of the available complex crystal structures. The residues from each of these hypervariable regions are noted below. Unless otherwise denoted, Kabat numbering according to the Kabat Database of aligned sequences of proteins will be employed (Wu and Kabat 1970 J. Exp. Med. 132:211-250; Johnson and Wu 2000 Nuc. Acids Res. 28(1):214-218). Hypervariable region or "Complementarity Determining Regions" locations are generally as follows: amino acids 24-34 ($V_L$ CDR-L1), amino acids 49-56 ($V_L$ CDR-L2), amino acids 89-97 ($V_L$ CDR-L3), amino acids 26-35A ($V_H$ CDR-H1), amino acids 49-65 ($V_H$ CDR-H2), and amino acids 93-102 ($V_H$ CDR-H3). Hypervariable regions may also comprise "extended hypervariable regions", amino acids 24-36 for the $V_L$ CDR-L1 and amino acids 46-56 for the $V_L$ CDR-L2. The variable domain residues are numbered according to Kabat et al 1991, supra for each of these definitions. An "altered hypervariable region" for the purposes herein is a hypervariable region comprising one or more (e.g. one to about 16) amino acid substitution(s) therein. An "un-modified hypervariable region" for the purposes herein is a hypervariable region having the same amino acid sequence as a non-human antibody from which it was derived, i.e. one that lacks one or more amino acid substitutions therein.

The terms "variable domain residue numbering as in Kabat", "amino acid position numbering as in Kabat", and variations thereof, refer to the numbering system used for heavy chain variable domains or light chain variable domains of the compilation of antibodies in Kabat et al 1991 supra). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Framework" or "FR" residues are those variable domain residues other than the hypervariable region residues as herein defined. A "human consensus framework" is a framework that represents the most commonly occurring amino acid residue in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al 1991 Sequences of Proteins of Immunological Interest, 5th Ed. Public Health Service, National Institutes of Health, Bethesda, Md.). In one embodiment, for the $V_L$, the subgroup is subgroup kappa I as in Kabat et al 1991. In one embodiment, for the $V_H$, the subgroup is subgroup III as in Kabat et al A "$V_H$ subgroup III consensus framework" comprises the consensus sequence obtained from the amino acid sequences in variable heavy subgroup III of Kabat et al 1991. A "$V_L$ subgroup I consensus framework" comprises the consensus sequence obtained from the amino acid sequences in variable light kappa subgroup I of Kabat et al 1991.

An "affinity matured" antibody is one with one or more alterations in one or more CDRs thereof which result in an improvement in the affinity of the antibody for antigen, compared to an antibody which does not possess those alteration(s). Affinity matured antibodies will have nanomolar or even picomolar affinities for the target antigen. Affinity matured antibodies are produced affinity maturation by VH and VL domain shuffling (Marks et al 1992 Bio/Technology 10:779-783), or random mutagenesis of CDR and/or framework residues (Barbas et al 1994 Proc Nat. Acad. Sci, USA 91:3809-3813; Schier et al 1995 Gene 169:147-155; Yelton et al 1995 J. Immunol 155:1994-2004; Jackson et al 1995 J. Immunol. 154(7):3310-9; and Hawkins et al 1992 J. Mol. Biol. 226:889-896).

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. The Fv polypeptide further comprises a polypeptide linker between the $V_H$ and $V_L$ domains that enables the scFv to form the desired structure for antigen binding (Plückthun 1994 The Pharmacology of Monoclonal Antibodies 113, Rosenburg and Moore eds., Springer-Verlag, New York, pp. 269-315).

The term "diabodies" refers to small antibody fragments with two antigen-binding sites, which fragments comprise a $V_H$ connected to a $V_L$ in the same polypeptide chain ($V_H$-$V_L$). By using a linker that is too short to allow pairing between the two domains on the same chain, the domains are forced to pair with the complementary domains of another chain and create two antigen-binding sites (EP 404,097; WO 1993/11161; Hollinger et al 1993 Proc. Natl. Acad. Sci. USA 90:6444-6448).

The term "antibody-drug conjugate", or "immunoconjugates" comprise an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

A "free cysteine amino acid" refers to a cysteine amino acid residue that has been engineered into a parent antibody, has a thiol functional group (—SH), and is not paired as, or otherwise part of, an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine-engineered antibody that reacts with a thiol-reactive reagent, and converted to a maximum value of 1. For example, a free cysteine amino acid on a cysteine-engineered antibody that reacts in 100% yield with a thiol-reactive reagent, such as a biotin-maleimide reagent, will form a biotin-labelled antibody that has a thiol reactivity value of 1.0. Another cysteine amino acid engineered into the same or different parent antibody that reacts in 80% yield with a thiol-reactive reagent will have a thiol reactivity value of 0.8. Another cysteine amino acid engineered into the same or different parent antibody that fails totally to react with a thiol-reactive reagent have a thiol reactivity value of 0. Determination of the thiol reactivity value of a particular cysteine may be conducted by ELISA assay, mass spectroscopy, liquid chromatography, autoradiography, or other quantitative analytical tests. Thiol-reactive reagents which allow capture of the cysteine-engineered antibody and comparison and quantitation of the cysteine reactivity include biotin-PEO-maleimide ((±)-biotinyl-3-maleimidopropionamidyl-3,6-dioxaoctainediamine, Oda et al 2001 Nature Biotechnology 19:379-382, Pierce Biotechnology, Inc.) Biotin-BMCC, PEO-Iodoacetyl Biotin, Iodoacetyl-LC-Biotin, and Biotin-HPDP (Pierce Biotechnology, Inc.), and Nα-(3-maleimidylpropionyl)biocytin (MPB, Molecular Probes, Eugene, Oreg.). Other commercial sources for biotinylation, bifunctional and multifunctional linker reagents include Molecular Probes, Eugene, Oreg., and Sigma, St. Louis, Mo.

An antibody or an antibody-drug conjugate is "internalized" when, after forming a complex with a cell surface antigen, the antigen-antibody complex or the antigen-antibody-drug conjugate complex present on the cell surface membrane is removed from the surface of the cell and incorporated into the cell itself via a biochemical reaction. Several possible post-endocytic trafficking pathways may thereafter engage the complex. (See reviews Schroeder et al 2001 "Recent advances in membrane microdomains: rafts, caveolae, and intracellular cholesterol trafficking." Exp Biol. Med (Maywood) November; 226(10):873-90), Spooner et al 2006 "Retrograde transport pathways utilized by viruses and protein toxins" Virol J. 2006; 3: 26) Antibodies prepared against denatured protein would be useful in Western blots, but would not be expected to bind cell surface epitopes nor form antigen-antibody complexes and thus would not be internalized.

The terms "Fc receptor" or "FcR" mean a receptor that binds to the Fc constant region of an antibody. Moreover, an FcR is one that binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See review Dacron 1997 Annu. Rev. Immunol. 15:203-234). FcRs are reviewed in Ravetch and Kinet 1991 Annu. Rev. Immunol 9:457-92; Capel et al 1994 Immunomethods 4:25-34; and de Haas et al 1995 J. Lab. Clin. Med. 126:330-41. Other FcRs, including those to be identified in the future, are encompassed by the term "FcR" herein. The term also includes the neonatal receptor, FcRn, which is responsible for the transfer of maternal IgGs to the fetus (Guyer et al 1976 J. Immunol. 117:587 and Kim et al 1994 J. Immunol 24:249).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen (Gazzano-Santoro et al 1996 J. Immunol. Methods 202:163).

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet 1991 Annu. Rev. Immunol. 9:457-92. To assess ADCC activity of a molecule of interest, an in vitro ADCC assay, such as that described in U.S. Pat. No. 5,500,362 and U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al 1998 Proc. Nat. Acad. Sci. USA 95:652-656.

"Human effector cells" are leukocytes that express one or more constant region receptors (FcRs) and perform effector functions. The cells express at least FcγRIII and perform ADCC effector function. Examples of human leukocytes that mediate ADCC include peripheral blood mononuclear cells (PBMC), natural killer (NK) cells, monocytes, cytotoxic T cells and neutrophils. The effector cells may be isolated from a native source thereof, e.g., from blood or PBMCs.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a cancer if, after receiving a therapeutic amount of an antibody, or antibody-drug conjugate thereof, according to the methods of the present invention, the patient shows observable and/or measurable reduction in or absence of one or more of the following: reduction in the number of cancer cells or absence of the cancer cells; reduction in the tumor size; inhibition (i.e., slow to some extent or stop) of cancer cell infiltration into peripheral organs including the spread of cancer into soft tissue and bone; inhibition of tumor metastasis; inhibition of tumor growth; and/or relief to some extent, one or more of the symptoms associated with the specific cancer; reduced morbidity and mortality, and improvement in quality of life issues. To the extent the antibody, or antibody-drug conjugate thereof, may prevent growth and/or kill existing cancer cells, it may be cytostatic and/or cytotoxic. The parameters for assessing successful treatment and improvement in the disease are readily measurable by routine procedures familiar to a physician. For cancer therapy, efficacy can be measured by, for example, assessing the time to disease progression (TTP) and/or determining the response rate (RR). Metastasis can be determined by staging tests and by bone scan and tests for calcium level and other enzymes to determine spread to the bone. CT scans can also be used to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

The terms "cancer" and "cancerous" refer to or describe the physiological condition in mammals that is typically characterized by unregulated cell growth. A "tumor" comprises one or more cancerous cells, and refers to all neoplastic cell growth and proliferation, whether malignant or benign, and all pre-cancerous and cancerous cells and tissues. Examples of cancer include, but are not limited to, carcinoma, lymphoma, blastoma, sarcoma, and leukemia or lymphoid malignancies. More particular examples of such cancers include colon cancer, squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, medulloblastoma, cervical cancer, ovarian cancer, liver cancer, bladder cancer, hepatoma, breast cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, and melanoma.

A cancer that "overexpresses" a polypeptide is one that has significantly higher levels of the polypeptide at the cell surface thereof, compared to a noncancerous cell of the same tissue type. Such overexpression may be caused by increased transcription or translation that in turn may have been caused by abnormalities or changes at the genetic level (e.g. DNA mutations or alterations), mRNA splice variations, or alterations in the activity of particular genetic transcription factors, promoters or enhancers. Overexpression may be determined in a diagnostic or prognostic assay by evaluating increased levels of the receptor protein present on the surface of a cell (e.g., via an immunohistochemistry assay; IHC). Alternatively, or additionally, one may measure levels of receptor-encoding nucleic acid in the cell, e.g., via fluorescent in situ hybridization (FISH; see WO 1998/45479), southern blotting, or polymerase chain reaction (PCR) techniques, such as real time quantitative reverse-transcriptase PCR (qRT-PCR).

The terms “cell proliferative disorder” and “proliferative disorder” refer to disorders that are associated with some degree of abnormal cell proliferation. In one embodiment, the cell proliferative disorder is cancer.

The term “therapeutically effective amount” refers to an amount of a drug effective to treat a disease or disorder in a mammal. In the case of cancer, the therapeutically effective amount of the drug may reduce the number of cancer cells; reduce the tumor size; inhibit (i.e., slow to some extent or stop) cancer cell infiltration into peripheral organs; inhibit tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The term “cytostatic” refers to the effect of limiting the function of cells, such as limiting cellular growth or proliferation of cells. For example in cancer therapy, efficacy can be measured by assessing the time to disease progression (TTP) and/or determining the response rate (RR).

The term “label” means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

The phrase “pharmaceutically acceptable salt,” as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate or tartrate salts. A pharmaceutically acceptable salt may involve the inclusion of another molecule such as an acetate ion, a succinate ion or other counterion. The counterion may be any organic or inorganic moiety that stabilizes the charge on the compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

“Pharmaceutically acceptable solvate” refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

“Carriers” as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

Compositions and Methods

HER4 Isoforms

Four structurally and functionally different isoforms are generated from a single HER4 gene by alternative splicing (18, 19). Two of the isoforms differ in the intracellular cytoplasmic domain (isoforms CYT-1 and CYT-2). CYT-1 has a 16 amino acid insert within the cytoplasmic domain while CYT-2 has no insert (18). The CYT-1 isoform can mediate coupling to phosphoinositide 3-kinase (PI3-K), but the CYT-2 isoform cannot (20, 21).

The other two isoforms (JM-a and JM-b) differ by an insertion of either 23 or 13 alternative amino acids in the extracellular juxtamembrane region (FIG. 1). JM-a is the isoform with 23 amino acids within the juxtamembrane region (NGPTSHDCIYYPWTGHSTLPQHA SEQ ID NO:1) while JM-1b is the isoform with 13 amino acids in this region (IGSSIEDCIGLMD SEQ ID NO:2) (17, 23).

The extracellular isoform JM-a can be cleaved by tumor necrosis factor-$\alpha$-converting enzyme (TACE) (22) whereas the JM-b isoform is proteinase-resistant (23). Cleavage by TACE triggers a second cleavage of HER4 involving $\gamma$-secretase activity (24). As a result the intracellular domain (ICD) is released from the cell membrane and translocates to the nucleus where it may function in regulating gene transcription (25-28).

Consistent with the hypothesis that HER4 isoforms differ in their role in tumorigenesis, the cleavable HER4 JM-a CYT-2 isoform, but not its non-cleavable counterpart JM-b CYT-2, demonstrates ligand-independent activity and promotes cancer cell growth (26). In addition, localization of an intracellular HER4 epitope in the nuclei is associated with shorter survival when compared to localization of HER4 at the cell surface (29) suggesting that HER4 cleavage can regulate tumor progression. These same cleavable isoforms have previously been shown to be overexpressed in a clinical series of breast cancer patient samples (18, 26).

Furthermore, the JM-a and JM-b isoforms exhibit different tissue distribution patterns as well with the isoform being absent from cardiac tissue (23).

Isoform Specific Antibodies

One aspect of the invention provides for an antibody that specifically binds to the JM-a isoform of HER4. In one embodiment, the antibody specifically binds to both the intact full-length HER4 receptor comprising the JM-a juxtamembrane region as well as the soluble HER4 ectodomain. In another embodiment, the antibody specifically binds to an amino acid sequence comprising NGPTSHD-CIYYPWTGHSTLPQHA SEQ ID NO:1. In another embodiment, the antibody specifically binds to the amino acid sequence NGPTSHDCIYYPWTGHSTLPQHA (SEQ ID NO:1).

Another aspect of the invention provides for an isolated anti-HER4 antibody that specifically binds to the HER4 JM-a isoform where the antibody is the mAb 1479 monoclonal antibody produced by the hybridoma cell line deposited with the ATCC having accession No. PTA-9655. In one embodiment, the antibody is a humanized or affinity matured antibody derived from the mAb 1479 monoclonal antibody produced by the hybridoma cell line deposited with the ATCC having accession No. PTA-9655.

Another aspect of the invention provides for an anti-HER4 antibody that comprises a fragment from the monoclonal antibody mAb 1479 produced by the hybridoma cell line deposited with the ATCC having accession No. PTA-9655. The antibody is specific for the JM-a isoform of HER4. In one embodiment, the fragment specifically binds to the HER4 JM-a isoform. In one embodiment, the fragment from mAb 1479 comprises at least a portion of the hypervariable region. In one embodiment, the fragment from mAb 1479 comprises the heavy chain hypervariable region. In one embodiment, the fragment from mAb 1479 comprises the light chain hypervariable region. In another embodiment, the fragment comprises the light and heavy chain hypervariable regions of mAb 1479. In one embodiment, the fragment comprises the VH1, VH2, or VH3 hypervariable region. In one embodiment, the fragment comprises at least two of the VH1, VH2, and VH3 hypervariable regions. In one embodiment, the fragment comprises all three of the VH1, VH2, and VH3 hypervariable regions. In one embodiment, the fragment comprises the VL1, VL2, or VL3 hypervariable region. In one embodiment, the fragment comprises at least two of the VL1, VL2, and VL3 hypervariable regions. In one embodiment, the fragment comprises all three of the VL1, VL2, and VL3 hypervariable regions. In one embodiment, the fragment comprises at least one, two, or three of the VH1, VH2, or VH3 hypervariable region and at least one, two, or three VL1, VL2, and VL3 hypervariable regions. In one embodiment, the fragment comprises all three of the VH1, VH2, or VL3 hypervariable region and all three of the VL1, VL2, and VL3 hypervariable regions.

In one embodiment, the fragment from mAb 1479 comprises at least a portion of the variable region. In one embodiment, the fragment from mAb 1479 comprises the heavy chain variable region. In one embodiment, the fragment from mAb 1479 comprises the light chain variable region. In another embodiment, the fragment comprises the light and heavy variable region of mAb 1479.

In some embodiments, the fragment comprises mutations that do not significantly decrease the binding specificity of the antibody for the JM-a isoform.

Another aspect of the invention provides for an antibody that competes for binding to the JM-a isoform with the anti-HER4 antibody mAb 1479 produced by the hybridoma cell line deposited with ATCC having accession No. PTA-9655.

Yet another aspect of the invention provides for an antibody that binds to the same epitope as the epitope to which the monoclonal antibody mAb 1479 produced by the hybridoma cell line deposited with the ATCC having accession No. PTA-9655 binds.

In one embodiment, the epitope bound by monoclonal antibody mAb 1479 comprises the HER4 ectodomain. In another embodiment, the epitope bound by monoclonal antibody mAb 1479 comprises at least a portion of the amino acid sequence NGPTSHDCIYYPWTGHSTLPQHA (SEQ ID NO:1). In another embodiment, the epitope bound by monoclonal antibody mAb 1479 comprises the amino acid sequence NGPTSHDCIYYPWTGHSTLPQHA (SEQ ID NO:1).

In some embodiments, the JM-a isoform specific antibodies are chimeric, human, or humanized antibodies.

In some embodiments, the anti-HER4 antibody that is specific for the JM-a isoform reduces HER4 tyrosine phosphorylation. Suppression of receptor tyrosine phosphorylation has been shown to be associated with anti-tumor activity of therapeutic antibodies targeting extracellular domains of other ErbB receptors (39, 48, 49). The effect of an anti-HER4 antibody on HER4 phosphorylation can be determined by methods well known in the art, one example of which is described herein in Examples 1 and 5. Briefly, cells expressing HER4 are treated with an anti-HER4 antibody then stimulated with NRG-1. The cells are lysed and immunoprecipitated with a general anti-HER4 antibody, such as HER-1 (R&D, Minneapolis, Minn.), separated in SDS-PAGE gels, and analyzed by Western blotting using an anti-phosphotyrosine antibody, such as 4G10 (Upstate Biotechnology, Lake Placid, N.Y.). The blots can be scanned and analyzed by scanning densitometry to provide a quantitative analysis. In some embodiments a control is included. In one embodiment, a control comprises a sample of cells expressing HER4 stimulated with NRG-1 in the absence of treatment with the anti-HER4 antibody. The cells are analyzed by Western blot as with the treated cells. In one embodiment, the anti-HER4 antibody reduces HER4 tyrosine phosphorylation by at least 30%, 40%, 50%, 60%, 70%, 80%, 85%, 90%, 95%, 96%, 97%, 98%, or 99%.

In some embodiments, the anti-HER4 antibody that is specific for the JM-a isoform reduces HER4 cleavage. Cleavage of HER4 results in the liberation of a 100 kDa ectodomain fragment. This event is also referred to as ectodomain shedding. The effect of an anti-HER4 antibody on HER4 cleavage can be determined by methods well known in the art, one example of which is described herein in Examples 1 and 5. Briefly, reduction in HER4 cleavage can be detected by determining the presence of the ectodomain in cell culture media of cells expressing HER4 treated with an anti-HER4 antibody. Cleavage can be enhanced by including phorbol 13-myristate 12-acetate (PMA) in the assay. In some embodiments a control is included. In one embodiment, a control is included wherein the presence of the ectodomain in cell culture media of cells expressing HER4 not treated with an anti-HER4 antibody is determined. In one embodiment, the anti-HER4 antibody reduces HER4 cleavage by at least 20%, 30%, 40%, 50%, 60%, 70%, 80%, 85%, 90%, 95%, 96%, 97%, 98%, or 99%.

In some embodiments, the anti-HER4 antibody that is specific for the JM-a isoform is internalized. Internalization of the antibody can be used to deliver antibody-conjugated toxins to cancerous cells that express HER4 JM-a isoform.

In some embodiments, the anti-HER4 antibody that is specific for the JM-a isoform promotes HER4 internalization. Internalization of tyrosine receptor kinases has been associated with downregulation of the receptors. In one embodiment, the anti-HER4 antibody decreases the amount of HER4 on the cell surface by at least 20%, 30%, 40%, 50%, 60%, 70%, 80%, 85%, 90%, 95%, 96%, 97%, 98%, or 99%. The effect of an anti-HER4 antibody on HER4 internalization can be determined by methods well known in the art, one example of which is described herein in Examples 1 and 6.

In some embodiments, the anti-HER4 antibody that specifically binds to the JM-a isoform of HER4 has less cardiotoxicity than an anti-HER4 antibody that is not specific for the HER4 JM-a isoform. Cardiotoxicity is a side-effect associated with many receptor tyrosine kinase inhibitor therapeutics (62, 63). Antibodies that are specific for the JM-a isoform of HER4 are predicted to produce less cardiotoxic effects in patients than anti-HER4 antibodies that recognize the JM-b isoform because the JM-a isoform is not present in cardiac tissue (23). Cardiotoxicity in a patient is evidenced by a number of symptoms including heart failure, Left Ventricular Dysfunction (LVD), myocardial ischemia, hypertension, venous thromboembolism, bradycardia, and QT interval (measure of the time between the start of the Q wave and the end of the T wave in the heart's electrical cycle) prolongation.

Cardiotoxicity of a compound can be measured, for example, by using in vitro or in vivo diagnostic models.

In vitro determination of cardiotoxicity can be made by exposing cardiac cells to a test compound and observing any changes in the cell appearance or cell apopotic rate. Relevant changes in cell appearance include mitochondirial swelling and degeneration. Cell apoptosis can be monitored by, for example, terminal deoxynucleotidyl transferase-mediated deoxyuridine 5-triphosphate nick end labeling. Additionally, the increased secretion of apoptic related chemicals or enzymes by the cells is indicative of cardiotoxicity. Such chemicals or enzymes include troponin, natriuretic peptides such as N-terminal propeptide of B-type (pro-BNP), cytochrome-C and caspase-9. Cardiac cells that can be used as the cultured cell model include primary or cultured adult or neonatal ventricular myocytes (cardiomyocytes) obtained from a suitable animal model, such as mouse or rat. (62-64).

In vivo determination of cardiotoxicity can be performed, for example, by injecting a test compound into a suitable animal model, such as a mouse or rat, and observing the effect of the test compound on the structure of the model's cardiac tissue, mitochondrial cardiac appearance and function, and/or on the model's cardiac tissue apoptosis rates (62). Isolated heart models, or Langendorf preps, are also useful for determining cardiotoxicity of compounds (63).

Cardiotoxicity can also be measured by clinical observations. For example, heart failure and LVD are measured by clinical diagnosis combining patient history and physical examination with diagnostic tests such as electrocardiogram (EKG), chest radiography, and multigated acquisition scan (MUGUA), Myocardial ischemia is determined by physical examination, detecting myocardial necrosis, detecting changes in EGK, and detecting increased elevations in cardiac enzymes. Hypertension is determined by measuring the blood pressure of a patient. Those patients with a blood pressure of greater or equal to 140/90 mm Hg are generally considered to have hypertension. Venous thromboembolism is detected by compression ultrasonography, tomography angiography, magnetic resonance pulmonary angiography, or nuclear medicine techniques. Bradycardia is generally defined as a heart rate of less than 60 beats per minute and is detected by determining the heart rate combined with an EKG or Holter monitor analysis. QT interval prolongation is an abnormality of the electrical activity of the heart and can be determined by EKG analysis. In general, a QT interval of less than or equal to 440 milliseconds is considered normal while a QT interval of greater than 450 milliseconds in men and 470 milliseconds in women is generally considered prolonged. (64).

Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the *facile* production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the socalled "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) J. Immunol 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies. See, e.g., Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human antibodies of the invention can be constructed by combining Fv clone variable domain sequence(s) selected from human-derived phage display libraries with known human constant domain sequence(s) as described above. Alternatively, human monoclonal antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci USA, 90: 2551 (1993); Jakobovits et al., Nature, 362: 255 (1993); Bruggermann et al., Year in Immunol., 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for the HER4 JM-a isoform and the other is for any other antigen. In certain embodiments, bispecific antibodies may bind to two different epitopes of the HER4 JM-a isoform. Bispecific antibodies may also be used to localize cytotoxic agents to cells which express the HER4 JM-a isoform. These antibodies possess a the HER4 JM-a isoform-binding arm and an arm which binds a cytotoxic agent, such as, e.g., saporin, anti-interferon-α, *vinca* alkaloid, ricin A chain, methotrexate or radioactive isotope hapten. Bispecific antibodies can be prepared as full length antibodies or antibody fragments (e.g. F(ab')2 bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) TIBTECH 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, the invention contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fç RIII only, whereas monocytes express Fç RI, Fç RII and Fç RIII. FcR expression on hematopoietic cells is summarized in Table 3 on page 464 of Ravetch and Kinet, Annu. Rev. Immunol. 9:457-92 (1991). Non-limiting examples of in vitro assays to assess ADCC activity of a molecule of interest is described in U.S. Pat. No. 5,500,362 (see, e.g. Hellstrom, I., et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. To assess complement activation, a CDC assay may be performed (see, for example, Gazzano-Santoro et al., J. Immunol Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, for example, Petkova, S. B. et al., Int'l. Immunol. 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 1, or as further described below in reference to amino acid classes Amino acid substitutions may be introduced into an antibody of interest and the products screened, e.g., for a desired activity, such as improved antigen binding, decreased immunogenicity, improved ADCC or CDC, etc.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) lion-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter, Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol 117:587 (1976) and Kim et al., J. Immunol 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogic et al. J. Immunol. 164: 4178-4184 (2000).

In another aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region.

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Certain Methods of Making Antibodies

Certain Hybridoma-Based Methods

Monoclonal antibodies of the invention can be made using the hybridoma method first described by Kohler et al., Nature, 256:495 (1975), and further described, e.g., in Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in:

Monoclonal Antibodies and T-Cell Hybridomas 563-681 (Elsevier, N. Y., 1981), and Ni, Xiandai Mianyixue, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, Histology and Histopathology, 20(3):927-937 (2005) and Vollmers and Brandlein, Methods and Findings in Experimental and Clinical Pharmacology, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide comprising the HER4 JM-a isoform, or a fragment thereof, and an adjuvant, such as monophosphoryl lipid A (MPL)/trehalose dicrynomycolate (TDM) (Ribi Immunochem. Research, Inc., Hamilton, Mont.). A polypeptide comprising the HER4 JM-a isoform or a fragment thereof may be prepared using methods well known in the art, such as recombinant methods, some of which are further described herein. Serum from immunized animals is assayed for anti-HER4 JM-a isoform antibodies, and booster immunizations are optionally administered. Lymphocytes from animals producing anti-HER4 JM-a isoform antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, Monoclonal Antibodies: Principles and Practice, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., Trends in Biotechnology, 24(3), 105-108 (2006).

Oligopeptides as tools for improving productivity of hybridoma cell cultures are described in Franek, Trends in Monoclonal Antibody Research, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to the HER4 JM-a isoform. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., Anal. Biochem., 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, DMEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in Methods in Molecular Biology 178:1-37 (O'Brien et al., ed., Human Press, Totowa, N. J., 2001). For example, one method of generating antibodies of interest is through the use of a phage antibody library as described in Lee et al., J. Mol. Biol. (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-HER4 JM-a isoform clones is desired, the subject is immunized with the HER4 JM-a isoform to generate an antibody response, and spleen cells and/or circulating B cells other peripheral blood lymphocytes (PBLs) are recovered for library construction. In a preferred embodiment, a human antibody gene fragment library biased in favor of anti-HER4 JM-a isoform clones is obtained by generating an anti-HER4 JM-a isoform antibody response in transgenic mice carrying a functional human immunoglobulin gene array (and lacking a functional endogenous antibody production system) such that HER4 JM-a isoform immunization gives rise to B cells producing human antibodies against the HER4 JM-a isoform. The generation of human antibody-producing transgenic mice is described below.

Additional enrichment for anti-HER4 JM-a isoform reactive cell populations can be obtained by using a suitable screening procedure to isolate B cells expressing the HER4 JM-a isoform-specific membrane bound antibody, e.g., by cell separation using affinity chromatography or adsorption of cells to fluorochrome-labeled HER4 JM-a isoform followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which the HER4 JM-a isoform is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about 1012 clones). Both vectors contain in vivo recombination signals so that the VH and VL genes are recombined onto a single replicon and are co-packaged into phage virions. These huge libraries provide large numbers of diverse antibodies of good affinity (Kd-1 of about 10-8 M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity (Kd-1 of about 106 to 107 M-1), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities of about 10-9 M or less.

Screening of the libraries can be accomplished by various techniques known in the art. For example, the HER4 JM-a isoform can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized the HER4 JM-a isoform under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci USA, 88: 7978-7982 (1991), or by alkali, e.g. as described in Marks et al., J. Mol. Biol., 222: 581-597 (1991), or by antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for the HER4 JM-a isoform. However, random mutation of a selected antibody (e.g. as performed in some affinity maturation techniques) is likely to give rise to many mutants, most binding to antigen, and a few with higher affinity. With limiting HER4 JM-a isoform, rare high affinity phage could be competed out. To retain all higher affinity mutants, phages can be incubated with excess biotinylated HER4 JM-a isoform, but with the biotinylated HER4 JM-a isoform at a concentration of lower molarity than the target molar affinity constant for HER4 JM-a isoform. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-HER4 JM-a isoform clones may be selected based on activity. In certain embodiments, the invention provides anti-HER4 JM-a isoform antibodies that bind to living cells that naturally express the HER4 JM-a isoform. In one embodiment, the invention provides anti-HER4 JM-a isoform antibodies that block the binding between HER4 JM-a isoform and a HER4 ligand, such as neuregulin, but do not block the binding between a neuregulin and a second protein. Fv clones corresponding to such anti-HER4 JM-a isoform antibodies can be selected by (1) isolating anti-HER4 JM-a isoform clones from a phage library as described above, and optionally amplifying the isolated population of phage clones by growing up the population in a suitable bacterial host; (2) selecting HER4 JM-a isoform and a second protein against which blocking and non-blocking activity, respectively, is desired; (3) adsorbing the anti-HER4 JM-a isoform phage clones to immobilized HER4 JM-a isoform; (4) using an excess of the second protein to elute any undesired clones that recognize HER4 JM-a isoform-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-HER4 JM-a isoform antibody derived from a hybridoma of the invention can also be modified, for example, by substituting the coding sequence for human heavy- and light-chain constant domains in place of homologous murine sequences derived from the hybridoma clone (e.g. as in the method of Morrison et al., Proc. Natl. Acad. Sci. USA, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Vectors, Host Cells, and Recombinant Methods

Antibodies may also be produced using recombinant methods. For recombinant production of an anti-HER4 JM-a isoform antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, αfactor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximinc (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fe effector function are not needed, such as when the therapeutic antibody is conjugated to a cytotoxic agent (e.g., a toxin) that by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, Methods in Molecular Biology, Vol. 248 (B. K. C. Lo, ed., Humana Press, Totowa, N. J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyccs occidentalis*; and filamentous fungi such as, e.g., *Neurospora, Penicillium, Tolypocladium*, and *Aspergillus* hosts such as *A. nidulans* and *A. niger*. For a review discussing the use of yeasts and filamentous fungi for the production of therapeutic proteins, see, e.g., Gerngross, Nat. Biotech. 22:1409-1414 (2004).

Certain fungi and yeast strains may be selected in which glycosylation pathways have been "humanized," resulting in the production of an antibody with a partially or fully human glycosylation pattern. See, e.g., Li et al., Nat. Biotech. 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, duckweed (Lemnaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N. J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol Meth. 62:1-13 (1983)). Protein G is recommended for all mouse isotypcs and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

In general, various methodologies for preparing antibodies for use in research, testing, and clinical are well-established in the art, consistent with the above-described methodologies and/or as deemed appropriate by one skilled in the art for a particular antibody of interest.

Immunoconjugates

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) Curr. Opinion in Pharmacology 5:543-549; Wu et al (2005) Nature Biotechnology 23(9):1137-1146; Payne, G. (2003) i 3:207-212; Syrigos and Epenetos (1999) Anticancer Research 19:605-614; Niculescu-Duvaz and Springer (1997) Adv. Drug Deliv. Rev. 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., Lancet (Mar. 15, 1986) pp. 603-05; Thorpe (1985) "Antibody Carriers Of Cytotoxic Agents In Cancer Therapy: A Review," in Monoclonal Antibodies '84: Biological And Clinical Applications (A. Pinchera et al., eds) pp. 475-506. Both polyclonal antibodies and monoclonal antibodies have been reported as useful in these strategies (Rowland et al., (1986) Cancer Immunol. Immunother. 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnol. 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include 212Bi, 131I, 131In, 90Y, and 186Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis-(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma 1I$, $\alpha 2I$, $\alpha 3I$, N-acetyl-$\gamma 1I$, PSAG and $\theta I1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$\text{Ab-(L-D)}_p \qquad 1$$

The linker may be composed of one or more linker components. Exemplary linker components include 6-malcimidocaproyl ("MC"), malcimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC'), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Therapeutic Uses

The antibodies described herein can be used for the treatment of cancer, including pre-cancerous, non-metastatic, and cancerous tumors (e.g., early stage cancer), or for the treatment of a subject at risk for developing cancer, for example, breast cancer. The antibodies and antibody fragments can also be used to treat or prevent non-malignant diseases, such as autoimmune and neurological disorders.

The antibodies that are specific for the JM-a isoform find particular utility in treating cancers or other disorders characterized by expression of the JM-a isoform. In one embodiment, the JM-a isoform is expressed in the cancer cells at a higher level than in non-cancerous cells of the same cell type or in non-cancerous cells adjacent to the cancerous cells. In some embodiments, the JM-a isoform is expressed at levels that are least 5%, 10%, 15%, 20%, 25%, 30%, 35%, 40%, 45%, 50%, 55%, 60%, 65%, 70%, 75%, 80%, 85%, 90%, or 95% higher than expression levels in the non-cancerous cells.

The antibodies that are specific for the JM-a isoform find particular utility in treating cancers or other disorders characterized by an increased level of shed HER4 ectodomain. As presented in the Examples, a series of histologically normal breast tissue and breast cancer tissue samples collected from the same patient demonstrated that the release of soluble HER4 ectodomain was significantly increased in the breast cancer when compared to the matched normal control tissue. Furthermore, nuclear localization of an intracellular HER4 epitope associates with unfavorable clinical outcome when compared to membranous HER4 expression, indicating that enhanced HER4 cleavage is associated with poor survival (29). In one embodiment, the level of shed HER4 ectodomain present in the cancer cells is at a higher level than in non-cancerous cells of the same cell type or in non-cancerous cells adjacent to the cancerous cells. In some embodiments, the level of shed HER4 ectodomain is at least 5%, 10%, 15%, 20%, 25%, 30%, 35%, 40%, 45%, 50%, 55%, 60%, 65%, 70%, 75%, 80%, 85%, 90%, or 95% higher than the level of shed HER4 ectodomain in non-cancerous cells.

Particular examples of cancers that overexpress the JM-a isoform and/or have increased levels of shed HER4 ectodomain include breast cancer, ovarian cancer, and medulloblastoma (15) (60). Cancers with increased levels of HER4 mutations are also expected to respond favorably to treatment with the antibodies that specifically bind to the HER4 JM-a isoform. Such cancers include lung cancer and melanoma (65) (66).

In some aspects of the invention, a patient is selected for treatment with an antibody that is specific for the JM-a isoform based on determining that the patient has a cancer or other disorder characterized by expression or overexpression of the JM-a isoform. As discussed in detail in the following Diagnostic Methods section, expression of the HER4 JM-a isoform can be detected using a number of methods including methods that detect the presence of JM-a isoform polypeptide, the presence of JM-a isoform polynucleotide, or the presence of shed HER4 ectodomain.

Diagnostic Methods

Another aspect of the invention provides for methods of determining the presence of the HER4 JM-a isoform. In one embodiment, the presence of the HER4 JM-a isoform is determined by detecting expression of the JM-a isoform. In one embodiment, expression of the HER4 JM-a isoform is determined by detecting the presence of JM-a isoform polypeptide. In one embodiment, expression of the HER4 JM-a isoform is determined by detecting the presence of JM-a isoform polynucleotide. In another embodiment, expression of the HER4 JM-a isoform is determined by detecting the presence of shed HER4 ectodomain.

A variety of methods for detecting expression of the HER4 JM-a isoform polypeptide and/or the presence of shed HER4 ectodomain can be employed and include, for example, immunohistochemical analysis, immunoprecipitation, Western blot analysis, molecular binding assays, ELISA, ELIFA, fluorescence activated cell sorting (FACS) and the like. For example, an optional method of detecting the expression of HER4 JM-a isoform polypeptide and/or shed HER4 ectodomain in a tissue or sample comprises contacting the sample with an antibody specific for the HER4 JM-a isoform, a HER4 JM-a isoform binding fragment thereof, or a recombinant protein containing an antigen binding region of a HER4 JM-a isoform specific antibody; and then detecting the binding of HER4 JM-a isoform polypeptide or shed HER4 ectodomain in the sample.

In particular embodiments of the invention, the expression of HER4 JM-a isoform polypeptide or presence of shed HER4 ectodomain in a sample is examined using immunohistochemistry and staining protocols Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods.

For sample preparation, a tissue or cell sample from a mammal (typically a human patient) may be used. Examples of samples include, but are not limited to, tissue biopsy, blood, lung aspirate, sputum, lymph fluid, etc. The sample can be obtained by a variety of procedures known in the art including, but not limited to surgical excision, aspiration or biopsy. The tissue may be fresh or frozen. In one embodiment, the sample is fixed and embedded in paraffin or the like.

The tissue sample may be fixed (i.e. preserved) by conventional methodology (See e.g., "Manual of Histological Staining Method of the Armed Forces Institute of Pathology," 3rd edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

Optionally, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen (e.g., HER4 JM-a isoform) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but are not limited to, rare earth chelates (europium chelates), Texas Red, rhodamine, fluorescein, dansyl, Lissamine, umbelliferone, phycoerytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in *Current Protocols in Immunology*, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym*. (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylenc diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope, and staining intensity criteria, routinely used in the art, may be employed. As one example, staining intensity criteria may be evaluated as follows:

TABLE 2

| Staining Pattern | Score |
|---|---|
| No staining is observed in cells. | 0 |
| Faint/barely perceptible staining is detected in more than 10% of the cells. | 1+ |
| Weak to moderate staining is observed in more than 10% of the cells. | 2+ |
| Moderate to strong staining is observed in more than 10% of the cells. | 3+ |

In alternative methods, the sample may be contacted with an HER4 JM-a isoform specific antibody under conditions sufficient for an antibody-antigen complex to form, and then detecting said complex. The presence of the complex may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labelled antibody to a target antigen.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of antigen.

Variations on the forward assay include a simultaneous assay, in which both sample and labelled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target antigen in the sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the ETA, the fluorescent labelled antibody is allowed to bind to the first antibody-molecular marker complex. After washing off the unbound reagent, the remaining tertiary complex is then exposed to the light of the appropriate wavelength. The fluorescence observed indicates the presence of the molecular marker of interest Immunofluorescence and EIA techniques are both very well established in the art. However, other reporter molecules, such as radioisotope, chemiluminescent or bioluminescent molecules, may also be employed.

Methods of the invention further include protocols which examine the presence and/or expression of HER4 JM-a isoform mRNAs in a tissue or cell sample. Methods for the evaluation of mRNAs in cells are well known and include, for example, hybridization assays using complementary DNA probes (such as in situ hybridization using labeled riboprobes, Northern blot and related techniques) and various nucleic acid amplification assays (such as RT-PCR using complementary primers specific for HER4 JM-a isoform, and other amplification type detection methods, such as, for example, branched DNA, SISBA, TMA and the like).

Tissue or cell samples from mammals can be conveniently assayed for HER4 JM-a isoform mRNAs using Northern, dot blot or PCR analysis. For example, RT-PCR assays such as quantitative PCR assays are well known in the art. Such methods can include one or more steps that allow one to determine the levels of HER4 JM-a isoform mRNA in a biological sample (e.g. by simultaneously examining the levels a comparative control mRNA sequence of a "housekeeping" gene such as an actin family member). Specific protocols for determining the presence of HER4 JM-a isoform mRNA are described in Junttila, T. T., et al, Clin. Cancer Res. 2003:9:5346-5357 (19).

Material embodiments of this aspect of the invention include HER4 JM-a isoform primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of HER4 JM-a isoform polynucleotides in a sample and as a means for detecting a cell expressing HER4 JM-a isoform polypeptides. As will be understood by the skilled artisan, a great many different primers and probes may be prepared based on the sequences provided in herein and used effectively to amplify, clone and/or determine the presence and/or levels of HER4 JM-a isoform mRNAs.

Optional methods of the invention include protocols which examine or detect mRNAs, such as HER4 JM-a isoform mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, U.S. Pat. No. 5,445,934, and U.S. Pat. No. 5,807,522, Lockart, *Nature Biotechnology*, 14:1675-1680 (1996); Cheung, V. G. et al., Nature Genetics 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commerically available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from Genbank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

The expression of a HER4 JM-a isoform may also be assessed by examining gene deletion or gene amplification. Gene deletion or amplification may be measured by any one of a wide variety of protocols known in the art, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe. By way of example, these methods may be employed to detect deletion or amplification of HER4 JM-a isoform genes.

Expression of HER4 JM-a isoform in a tissue or cell sample may also be examined by way of functional or activity-based assays. For example, expression of HER4 JM-a isoform can be detected by determining the effect of treatment with tumor necrosis factor-alpha-converting enzyme (TACE) on tissue or cell samples suspected of expression HER4 JM-a isoform.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage, sterile injectable form. An antibody-drug conjugate (ADC) having the desired degree of purity is optionally mixed with pharmaceutically acceptable diluents, carriers, excipients or stabilizers (Remington: The Science and Practice of Pharmacy 21st edition (2005) ed. Univ. of the Sciences Philadelphia, Lippincott Williams & Wilkins), in the form of a lyophilized formulation or an aqueous solution.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 21st edition (2005) ed. Univ. of the Sciences Philadelphia, Lippincott Williams & Wilkins.

Sustained-release preparations may be prepared. Suitable examples of sustained-release preparations include semi permeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations include those suitable for the foregoing administration routes. The formulations may conveniently be presented in unit dosage form and may be prepared by any of the methods well known in the art of pharmacy. Techniques and formulations generally are found in Pharmaceutical Preformulation and Formulation: A Practical Guide from Candidate Drug Selection to Commercial Dosage Form. 1st edition (Aug. 1, 2001) Ed Mark Gibson, US Informa Healthcare, Marcel Dekker, CRC Press (ISBN-10 1574911201); Handbook of Pharmaceutical Excipients 5th edition (Dec. 14, 2005) Raymond C. Rowe, Paul J. Sheskey, and Siân C. Owen APhA Publications (ISBN-10: 1582120587).

Such methods include the step of bringing into association the active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are disfavored due to hydrolysis or denaturation in the gut, formulations suitable for oral administration may be prepared as discrete units such as capsules, cachets or tablets each containing a predetermined amount of the antibody.

The formulations may be packaged in unit-dose or multi-dose containers, for example scaled ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Unit dosage formulations are those containing a daily dose or unit daily sub-dose, as herein above recited, or an appropriate fraction thereof, of the active ingredient.

The compositions of the invention may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al 1985 Proc. Natl. Acad. Sci. USA 82:3688; Hwang et al 1980 Proc. Natl Acad. Sci. USA 77:4030; U.S. Pat. No. 4,485,045; U.S. Pat. No. 4,544,545; U.S. Pat. No. 5,013,556; WO 1997/38731. Liposomes can be generated by the reverse phase evaporation method with a lipid composition comprising phosphatidylcholine, cholesterol and PEG-derivatized phosphatidylethanolamine (PEG-PE). Liposomes may be extruded through filters of defined pore size to yield liposomes with the desired diameter. Fab' fragments of the compositions of the present invention can be conjugated to liposomes (Martin et al 1982 J. Biol. Chem. 257:286-288), via a disulfide interchange reaction. A chemotherapeutic agent is optionally contained within the liposome (Gabizon et al 1989 J. National Cancer Inst. 81(19): 1484.)

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above therapeutic methods may be carried out using an immunoconjugate of the invention in place of or in addition to an antibody.

Combination Therapy

An antibody of the invention may be combined in a pharmaceutical combination formulation, or dosing regimen as combination therapy, with a second compound having anti-cancer properties. The second compound of the pharmaceutical combination formulation or dosing regimen may have complementary activities to the antibody of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an antibody of the invention may also have a therapeutically effective amount of a chemotherapeutic agent such as a tubulin-forming inhibitor, a topoisomerase inhibitor, a DNA intercalator, or a DNA binder.

Other therapeutic regimens may be combined with the administration of an anticancer agent identified in accordance with this invention. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

Examples of such combination therapy include combinations with chemotherapeutic agents such as erlotinib (TARCEVA®, Genentech/OSI Pharm.), bortezomib (VELCADE®, Millenium Pharm.), fulvestrant (FASLODEX®, AstraZeneca), sutent (S U11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNE®, Wyeth), lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics, calicheamicin, calicheamicin gamma1I and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitracrine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylomithine (DMFO); retinoids such as retinoic acid; capecitabine; and pharmaceutically acceptable salts, acids or derivatives of any of the above.

Such combination therapy also includes: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON• toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors, such as for example inhibitors of the EGFR pathway (EGFR, HER2, HER3, and HER4); (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; (x) anti-angiogenic agents such as bevacizumab (AVASTIN®, Genentech); and (xi) pharmaceutically acceptable salts, acids or derivatives of any of the above.

Preparation and dosing schedules for such chemotherapeutic agents may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Articles of Manufacture

In another embodiment of the invention, an article of manufacture, or "kit", containing materials useful for the treatment of the disorders described above is provided. The article of manufacture comprises a container and a label or package insert on or associated with the container. The package insert may refer to instructions customarily included in commercial packages of therapeutic products and that contain information about the indications, usage, dosage, administration, contraindications and/or warnings concerning the use of such therapeutic products. Suitable containers include, for example, bottles, vials, syringes, blister pack, etc. The containers may be formed from a variety of materials such as glass or plastic.

In one embodiment, the article of manufacture comprises a container and a formulation of an anti-HER4 antibody, or antibody-drug conjugate thereof, contained within the container. The article may further optionally comprise a label affixed to the container, or a package insert included with the container, that refers to the use of the composition of matter for the therapeutic treatment or diagnostic detection of a tumor. The container holding the formulation is effective for storing and delivering the therapeutic and may have a sterile access port (for example the container may be an intravenous solution bag or a vial having a stopper pierceable by a hypodermic injection needle). The label or package insert indicates that the formulation is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Deposit of Material

The following materials have been deposited with the American Type Culture Collection, 10801 University Blvd., Manassas, Va. 20110-2209, USA (ATCC):

| Material | ATCC Dep. No. | Deposit Date |
|---|---|---|
| Her-4 1H10.1E5 | PTA-9655 | Dec. 11, 2008 |

This deposit was made under the provisions of the Budapest Treaty on the International Recognition of the Deposit of Microorganisms for the Purpose of Patent Procedure and the Regulations thereunder (Budapest Treaty). Access to the deposits will be available under the terms of the Budapest Treaty, and subject to an agreement between Genentech Inc. and ATCC, during the pendency of this application to persons determined by the Commissioner of Patents and Trademarks to be entitled thereto under 37 C.F.R. 1.14 and 35 U.S.C. 122. Upon allowance of any claims in this application, all restrictions on the availability to the public of the deposits will be irrevocably removed. The deposits will be maintained in the ATCC depository, which is a public depository, for a period of at least 30 years, or at least 5 years after the most recent request for a sample of the deposit, or for the enforceable life of the patent, whichever is longer, and will be replaced if a deposit becomes nonviable during that period.

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention.

All patent and literature references cited in the present specification are hereby expressly incorporated by reference in their entirety.

EXAMPLES

Example 1—Materials and Methods

Anti-HER4 Antibodies.

Specific oligonucleotides were synthesized on the basis of the HER4 DNA sequence (30). Total cellular RNA was extracted from MDA-MB-453 cells and used as a template in RT PCR, to generate the human HER4 extracellular domain (ECD) coding sequence.

A gDHER4 ECD fusion protein was constructed by ligating the coding sequences for amino acids 1-52 of herpes simplex virus type 1 glycoprotein D to the sequences encoding amino acids 26-640 of human HER4. (61) The gDHER4 ECD cDNA was inserted into the cytomegalovirus-based expression vector pRK5. This construct was transiently transfected into human embryonic kidney 293 cells using a standard calcium phosphate precipitation protocol.

An affinity column was prepared by coupling the anti-gD monoclonal 5B6 to CNBR sepharose (Pharmacia LKB Biotechnology, Uppsala Sweden). Supernatant from gDHER4 ECD transfected 293 cells was concentrated 20-40 fold on a ym30 membrane (Amicon, Beverly Mass.) and loaded onto the affinity resin. The column was washed with PBS and the receptor was eluted with 100 mM acetic acid/500 mM NaCl pH 2.4. The HER4 ECD was buffer exchanged into PBS and concentrated. Protein concentration was determined by OD280.

Balb/c mice were immunized with approximately 5 ug of HER4 ECD in RIBI MPL+TDM+CWS Emulsion (RIBI ImmunoChem Research Inc., Hamilton, Mont.) in their rear footpads on weeks 0, 1, 2 and 3. The immunized mice were tested for an antibody response by ELISA. The mice with the highest titers were given an additional 5 ug of HER4 ECD in RIBI during week 4. Three days later, the lymphocytes from the popliteal and inguinal nodes, were fused with mouse myeloma line X63-Ag8.653 using 50% polyethylene glycol 4000 (Boehringer Mannheim Corporation, Indianapolis, Ind.) by the procedure of Oi and Herzenberg, 1980. Fused cells were plated at a density of 200,000 cells per well in 96-well tissue culture plates and hybridoma selection using HAT media supplement (Sigma-Aldrich, St. Louis, Mo.) began one day post fusion. Beginning on day 10, the hybridoma supernatants were screened for the presence of HER4 specific antibodies using a radioactive capture assay. Stable antibody producing clones were obtained by limiting dilution and large quantities of specific mAbs were produced in ascites. The antibodies were purified on protein A-Sepharose columns (Fermentech, Inc., Edinburgh, Scotland) and stored sterile in PBS at 4° C.

Tissues.

Frozen sections of normal human heart and kidney were obtained from a four year old male died of an electric shock. Seventeen snap-frozen tissue sample pairs representing human breast cancer and histologically normal peripheral tissue from same patient were kindly provided by Dr. Manolo M. Morente, Spanish National Tumour Bank Network, Spanish National Cancer Centre (CNIO), Madrid, Spain. Use of all tissue samples was approved by an Institutional Review Board, and an informed consent was obtained from all study subjects.

Cell Culture.

COS-7, NIH 3T3-7d transfectants expressing EGFR, HER2 or HER3 (31) and HEK293 EBNA (Invitrogen, Carlsbad, Calif.) cells were maintained in DMEM, and T-47D and MCF-7 cells in RPMI, supplemented with 10% FCS (Autogen Bioclear UK Ltd., Wiltshire, UK) and 1% L-glutamine-penicillin-streptomycin solution (Sigma-Aldrich).

Plasmid Constructs.

The expression plasmids pcDNA3.1HER4JM-aCYT-2, pcDNA3.1HER4JM-bCYT-2, pcDNA3.1HER4JM-aCYT-2-HA and pcDNA3.1HER4JM-bCYT-2-HA (26, 32) were used to transiently express HER4 isoforms with or without carboxyterminal hemagglutinin (HA) epitope tags in COS-7 cells. To generate kinase dead HER4 construct the putative ATP binding site within the kinase domain of HER4 was mutated (K751R) in pcDNA3.1HER4JM-aCYT-2 using site-directed mutagenesis kit (Stratagene) to produce pcDNA3.1HER4JM-aCYT-2-K751R. To generate pcDNA3.1HER4ECD HER4 ectodomain encoding sequence was derived from full-length pcDNA3.1HER4JM-aCYT-1 (26) by PCR using 5'-primer TTG GTA CCG CAC CAT GAA GCC GGC GAC AGG AC (SEQ ID NO: 3) and 3'-primer T TAT CTC GAG TTA GTG ATG GTG ATG GTG ATG TTG TGG TAA AGT GGA ATG (SEQ ID NO: 4). The 5'-primer introduced a Kpn I restriction endonuclease recognition sequence and a ribosome binding sequence prior to start codon of HER4 sequence. The 3'-primer introduced a hexahistidine encoding sequence, a new stop codon and a Xho T endonuclease recognition sequence after the last extracellular amino acid His647 of HER4 JM-a (23).

Transfections.

Cells plated on 24-well plates (4×104) or 6-well plates (1.5×105) were transfected with 0.5-1 ug of appropriate plasmid using FuGENE 6 Transfection Reagent (Roche, Mannheim, Germany) according to manufacturer's protocol.

Production of Recombinant Extracellular Domain of HER4.

HEK293 EBNA cells transfected with pcDNA3.1 HER4ECD were selected in medium containing 150 ug/ml Hygromycin B (Roche) and after cloning maintained in the presence 75 ug/ml of Hygromycin B. Before recovering the soluble ectodomain from the medium, the cells were cultured in DMEM containing 0.5% FCS. The HIS-tagged ectodomain was purified from collected culture medium by immobilized metal chelate affinity chromatography (GE Healthcare, Chalfont St. Giles, UK) by stepwise pH gradient.

Immunoprecipitation and Western Blot Analyses.

To study isoform-specificity of monoclonal anti-HER4 antibodies, COS-7 cells were transiently transfected with pcDNA3.1HER4JM-aCYT-2, pcDNA3.1 HER4JM-bCYT-2, or pcDNA3.1 vector. Twenty-four hours later, the cells were washed with ice cold PBS, lysed in lysis buffer (1% Triton X-100, 10 mM Tris-HCL (pH 7.4), 1 mM EDTA, 2 mM phenylmethylsulfonyl fluoride, 10 ug/ml aprotinin, 10 ug/ml leupeptin, 1 mM sodium orthovanadate, 10 mM sodium fluoride, and 10 mM sodium phosphate) and centrifuged. The supernatants were either boiled or not at 95° C. for five minutes in sample buffer with or without dithiothreitol (DTT) and analyzed by SDS-PAGE and Western blotting, as previously described (21). ErbB expression in NIH 3T3-7d transfectants was analyzed by Western blotting under non-reducing conditions using the following primary antibodies: anti-EGFR (sc-03), anti-HER2 (sc-284), anti-HER3 (sc-285) (all from Santa Cruz Biotechnology, Santa Cruz, Calif.), and mAb 1479.

For Western analysis of HER4 protein in breast tissue, 80 um sections of frozen tissue blocks were cut, homogenized, and lysed in lysis buffer overnight at 4° C. in a shaker. Aliquots of lysates equivalent to 50 ug of total protein were analyzed by Western blotting under non-reducing conditions.

To study the effect of mAb 1479 on HER4 phosphorylation, MCF-7 and T-47D cells were starved overnight in RPMI without serum and treated with or without 1 ug/ml of mAb 1479 for one hour prior to 30 minute stimulation with 50 ng/ml neuregulin-1 (NRG-1; R&D, Minneapolis, Minn.). Cell lysates equivalent to 1 mg of total protein were immunoprecipitated with anti-HER4 antibody (HFR-1), separated in SDS-PAGE gels, and analyzed by Western blotting using anti-phosphotyrosine antibody (4G10; Upstate Biotechnology, Lake Placid, N.Y.).

To study HER4 ubiquitylation, COS-7 cells were transiently transfected with plasmids encoding full length JM-a CYT-1 or JM-a CYT-2 together with Flag-tagged ubiquitin (Katz et al. 2002), and analyzed by HER4 immunoprecipitation followed by anti-Flag Western blotting, as previously described (32). The cells were treated for one hour with or without 2 ug/ml mAb 1479 prior to analysis.

Immunofluorescence Staining.

COS-7 cells were grown on coverslips and transfected with pcDNA3.1HER4JM-aCYT-2-HA, pcDNA3.1HER4JM-bCYT-2-HA, or pcDNA3.1 vector control. Twenty-four hours after transfection cells were fixed with methanol, stained with anti-HER4 (HFR-1; Neomarkers, Fremont, Calif.) or anti-HA (Roche) in 1:100 dilution, followed by incubation with Alexa Fluor 488 goat anti-mouse or Alexa Fluor 568 goat anti-rat (both from Molecular Probes, Leiden, The Netherlands) in 1:250 dilution. Coverslips were mounted with Vectashield mounting medium (Vector Laboratories, Inc., Burlingame, Calif.). All images were obtained by Olympus BX60 (Olympus, Hamburg, Germany) fluorescence microscope.

Immunohistochemistry.

Frozen sections (5 uM) were stained using 20 ug/ml of primary antibodies mAb 1479, anti-HER4 (HFR-1), anti-CD44 (Hermes-3; kindly provided by Dr. Sirpa Jalkanen, University of Turku, Turku, Finland), or an antibody recognizing a chicken T-cell antigen (3g6; kindly provided by Dr. Sirpa Jalkanen), and secondary antibodies Alexa Fluor 488 goat anti-mouse (1:200) or HRP-conjugated goat anti-mouse (1:100; Santa Cruz Biotechnology). For peroxidase staining sections were treated with DAB peroxidase substrate (Vector Laboratories) according to manufacturer's instructions followed by staining with hematoxylin. For immunofluorescence staining sections were treated with 25 mg/ml of 1,4-diazabicyclo[2.2.2.]octan (Sigma-Aldrich) to prevent photobleaching. All slides were mounted with mowiol (Calbiochem) and visualized by Olympus BX60 fluorescence microscope.

In Vitro Binding Assay.

Recombinant HIS-tagged HER4 ectodomain (2 ug) was incubated with or without 0.5 ug mAb 1479 or 3g6. Complex formation between the ectodomain and other proteins was visualized by Western blotting with anti-penta HIS antibody (Molecular Probes) under non-reducing conditions.

Analysis of HER4 Cleavage.

To study the effect of mAb 1479 on HER4 cleavage, T-47D cells were starved for 2 hours without serum and treated for 1 hour with 1 μg/ml mAb 1479 prior to stimulating cleavage with 100 ng/ml phorbol 13-myristate 12-acetate (PMA; Sigma-Aldrich) (23, 33).

To study the effect of mAb 1479 on basal shedding of HER4 ectodomain into culture medium, COS-7 transiently expressing HER4 JM-a CYT-2 were treated with or without 1 ug/ml mAb 1479 or 1475 for twenty-four hours. Ectodomain shedding was analyzed from 60 ul of medium samples directly collected from cell culture dishes by Western blotting with anti-HER4 antibody mAb 1464.

HER4 Internalization.

COS-7 cells were grown on coverslips and transfected with pcDNA3.1HER4JM-aCYT-2 or kinase dead pcDNA3.1HER4JM-aCYT-2K751R (32) and Rab5a-GFP (34). Twenty-four hours after transfection the cells were treated for 5 mm or 2 hours with 1 ug/ml of mAb 1479. The cells were fixed with methanol and stained with Alexa Fluor 568 goat anti-mouse. Coverslips were mounted with Vectashield mounting medium. Images were obtained by LSM 510 Meta confocal microscope (Carl Zeiss, Inc., Thornwood, N.Y.)

MTS Proliferation Assay.

T-47D and MCF-7 cells were starved overnight and plated (1.5×104/well) on 96-well plates in RPMI containing 5% charcoal-stripped FCS and 1 ug/ml mAb 1479 or 10 ug/ml 2C4 (Genentech Inc., South San Francisco, Calif.). The number of viable cells was estimated at indicated time points with CellTiter 96® Non-Radioactive Cell Proliferation Assay (Promega, Madison, Wis.) following manufacturer's instructions.

Anchorage-Independent Growth Assay.

Bottom layers consisting of 2 ml RPMI, 0.5% Bacto agar, and 10% FCS were applied on 6-well plates. After solidification of the bottom layers, top layers consisting of 30,000 cells/well in 1.2 ml RPMI, 0.33% Bacto Agar, and 10% FCS with or without 1 ug/ml mAb 1479 were applied on top. All samples were prepared in triplicate. Cells were incubated for 14 days at 37° C. Colonies larger than 8 cells were counted under microscope.

Statistical Analysis.

Student's t-test was used for statistical analysis of different time points of MTS and soft agar assays. The analysis included five independent MTS and three independent soft agar experiments. The quantities of full-length HER4 and HER4 ectodomain in tumor vs. normal tissues were compared using matched tumor/normal tissue pairs with the Wilcoxon signed rank test.

Example 2—mAb 1479 Selectively Recognizes the Proteolytically Cleavable JM-a Isoforms of HER4

Twenty-nine hybridoma clones secreting antibodies against the ectodomain of HER4 were screened for selective recognition of HER4 isoforms (FIG. 2). Isotyping of the monoclonal antibodies was done using a Mouse MonoAb ID/SP isotyping kit from Zymed (Zymed, So. San Francisco, Calif.) according to the manufacturer's instructions. The epitope mapping was performed by a cross-blocking ELISA. The HER4 mAbs were grouped into epitopes based on their ability to block binding of the others by 50% or greater in comparison to an irrelevant mAb control. The specificity of the HER4 mAbs was determined in an ELISA by testing the ability of the biotinylated HER4 mAbs to bind HER2 (aa 1-645), HER3 (aa 1-617) and HER4 (aa 1-640) extracellular domains (Genentech, Inc.) coated on an ELISA plate at a concentration of 1 μg/ml.

Figure 3:
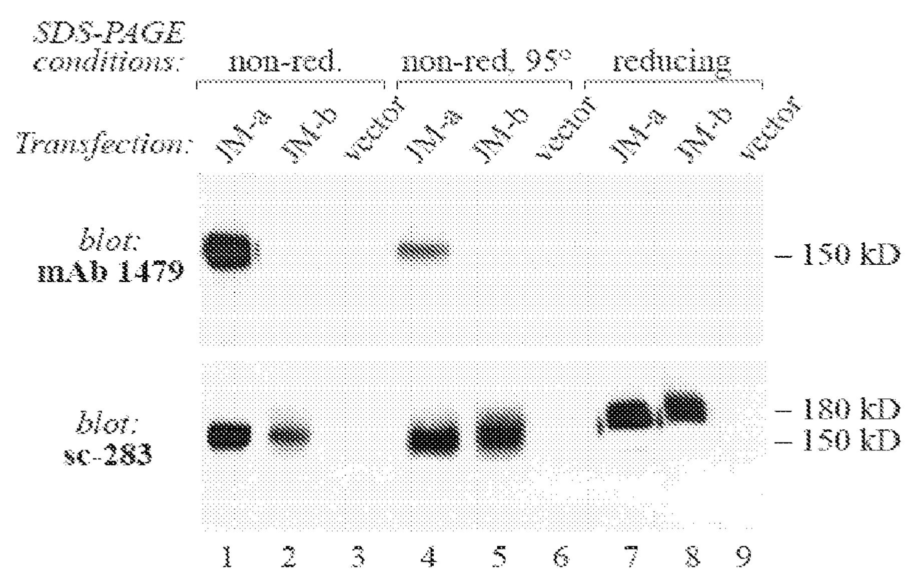
FIG. 3 is a Western blot analysis depicting the binding specificity of mAb 1479 and a control antibody, sc-283, for COS-7 cells expressing HER4 isoforms JM-a CYT-2 or JM-b CYT-1.

COS-7 cells transiently expressing HER4 isoforms with alternative extracellular juxtamembrane domains (JM-a CYT-2 or JM-b CYT-2) were analyzed. Western analysis was carried out in three conditions representing different degrees of protein denaturation (FIG. 3). Prior to SDS-PAGE, samples in lanes 1-3 of FIG. 3 were dissolved in sample buffer without DTT at room temperature (non-red.); samples in lanes 4-6 were dissolved in sample buffer without DTT but heated for 5 min at 95° C. (non-red., 95° C.); and samples in lanes 7-9 were dissolved in sample buffer containing DTT as well as heated for 5 min at 95° C. (reducing). Antibodies against the carboxy-terminus of HER4 (sc-283 and HFR-1) or against the HA-tag (anti-HA) were used to control transfection efficiency.

One of the antibodies, mAb 1479, recognized the JM-a isoform, but not the JM-b isoform, when used as the primary antibody in Western blotting (FIG. 3). The HER4-specific signal was reduced in intensity when samples were boiled prior to analysis, and totally abolished when samples were boiled as well as subjected to reducing conditions with DTT. This indicates that the mAb 1479 antibody only recognizes the native conformation. Under non-reducing conditions HER4 appeared as a band of 150 kD, close to the expected size of 144 kD deduced from cDNA (30), and under reducing conditions as a band of 180 kD (compare FIG. 3, bottom panel, lanes 1 vs. 7). The specificity of mAb 1479 for JM-a isoform was confirmed by immunofluorescence staining of COS-7 cells transiently expressing HA-tagged HER4 isoforms. mAb 1479 again recognized epitopes solely on the surface of JM-a-transfectants.

Figure 4:
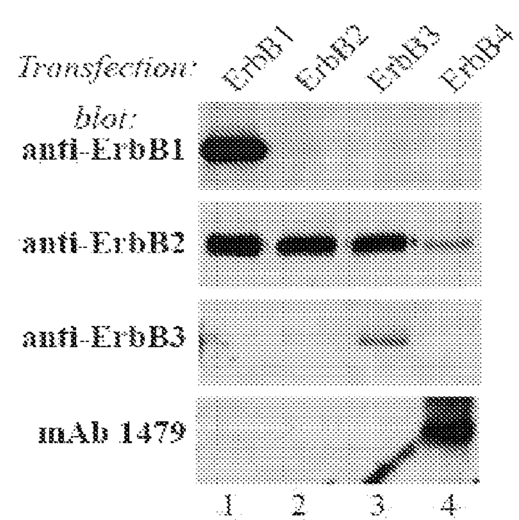
FIG. 4 is a Western blot analysis depicting the binding specificity of mAb 1479 and control antibodies anti-EGFR (sc-03), anti-HER2 (sc-284), anti-HER3 (sc-285) for NIH 3T3-7d and NR6 cells stably expressing different ErbB receptors.

As family members of the ErbB receptor are homologous, the cross-reactivity of mAb 1479 with other ErbB receptors was assessed by Western blotting using NIH 3T3-7d and NR6 transfectants stably expressing the different ErbB receptors (31). mAb 1479 gave a strong signal for HER4 (JM-a CYT-2), with faint band in western analysis from cells overexpressing EGFR (FIG. 4). In FIG. 4, parental (lane 2) or transfected (lanes 1 and 3) NIH 3T3-7d and NR6 (lane 4) cells expressing different ErbB receptors were analyzed by western blotting using anti-EGFR (sc-03), anti-HER2 (sc-284), anti-HER3 (sc-285) or mAb 1479 as the primary antibody. The parental NTH 3T3-7d and NR6 cells express endogenous HER2, which was detected in all analyzed transfectants with anti-HER2.

Figure 5:
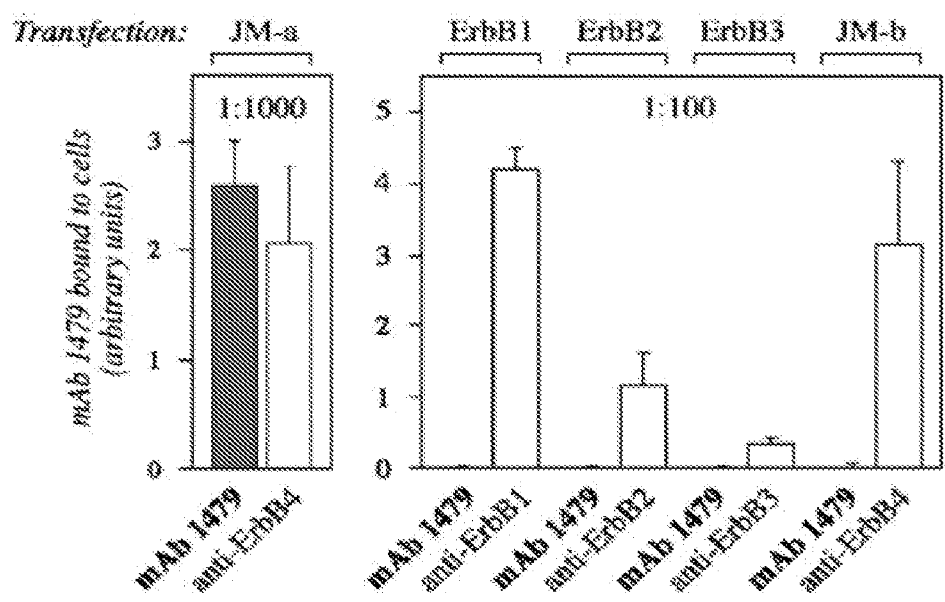
FIG. 5 is a graph showing the binding specificity of mAb 1479 for NIH 3T3-7d and NR6 transfectants expressing HER4 JM-a CYT-2, HER4 JM-b CYT-1, EGFR, HER2, or HER3 as analyzed by a cell enzyme-linked immunosorbent assay (ELISA) (gray columns). mAb 1479 binding was compared to binding of anti-EGFR (sc-03), anti-HER2 (sc-284), anti-HER3 (sc-285) and anti-HER4 (sc-283) (binding of all control antibodies in white columns) in dilutions 1:1000 (left) or 1:100 (right).

A cell-based enzyme-linked immunosorbent assay (ELISA) was used to further assay crossreactivity of mAB 1479. mAb 1479, as well as a positive control anti-HER4 antibody (sc-283), clearly bound to NR6 transfectants expressing HER4 (JM-a CYT-2) even at the lowest antibody concentrations (1:1000 1.25 ug/ml of mAB 1479; 0.2 ug/ml of sc-283) tested (FIG. 5). However, no binding of mAb 1479 was observed to NIH 3T3-7d cells expressing EGFR, HER2, or HER3, or the JM-b CYT-1 isoform of HER4 even at the highest antibody concentrated tested (1:100, 12.5 ug/ml), whereas the control antibodies anti-EGFR (sc-03), anti-HER2 (sc-284), anti-HER3 (sc-285), and anti-HER4 (sc-283) demonstrated binding (1:100, 2 ug/ml) (FIG. 5). These data indicate that mAb 1479 is specific for the JM-a isoform of HER4.

Example 3—mAb 1479 Recognizes the Shed Ectodomain of HER4

Figure 6:
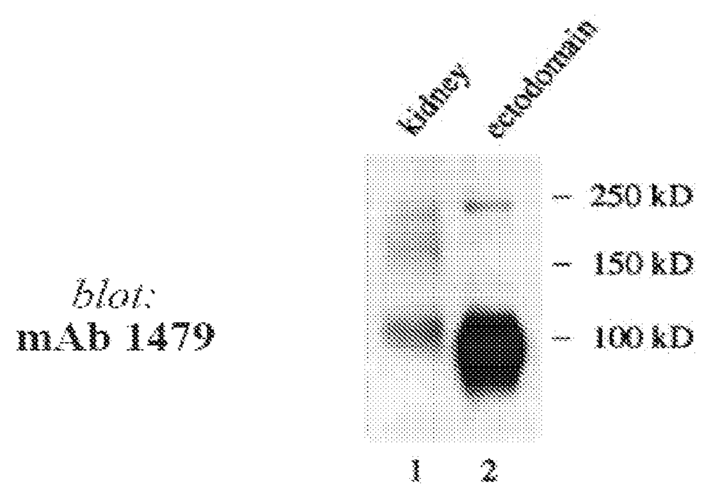
FIG. 6 is a Western blot analysis showing binding of mAb 1479 to shed HER4 ectodomain in human kidney tissue lysate and to recombinant HER4 ectodomain.

To address whether mAb 1479 can be used to selectively analyze expression of the HER4 JM-a isoforms in vivo, frozen sections of human kidney and heart were assessed by immunofluorescence staining. These two tissue types were selected as they have been shown to exclusively express either JM-a (kidney) or JM-b (heart) isoforms (23). As expected based on the in vitro specificity discussed in Example 2, mAb 1479 specifically stained kidney but not heart tissue. A positive control antibody against the carboxy-terminal end of HER4 (HFR-1) stained both tissues, and no immunostaining was observed when a negative control antibody against a chicken T-cell protein (3g6) was used. An antibody against the membrane-anchored CD44 protein was used to visualize the cell membrane compartment. The staining pattern observed for mAb 1479 differed from that observed for HFR-1. This can be explained by the different epitopes they recognize, but more likely by the fact that the HER4 molecule is cleaved and its ectodomain shed in kidney tissue, as suggested by localization of HER4 ICD in the nucleus of glomerular cells. Also in support of HER4 cleavage in kidney tissue in vivo, Western analysis of kidney tissue lysates demonstrated that mAb 1479 recognized two major bands (FIG. 6). One migrated at 150 kD corresponding to the size of full-length ErbB under non-reducing conditions (compare FIG. 6, lane 1 vs. FIG. 3, lane 1) and the other more prominent one at 100 kD corresponding to the size of recombinant HER4 ectodomain (FIG. 6, lanes 1 vs. 2). A third band migrating at about 200 kDa was similar in size to a weak band in the lane with recombinant ectodomain and represent ectodomain dimers.

Figure 7:
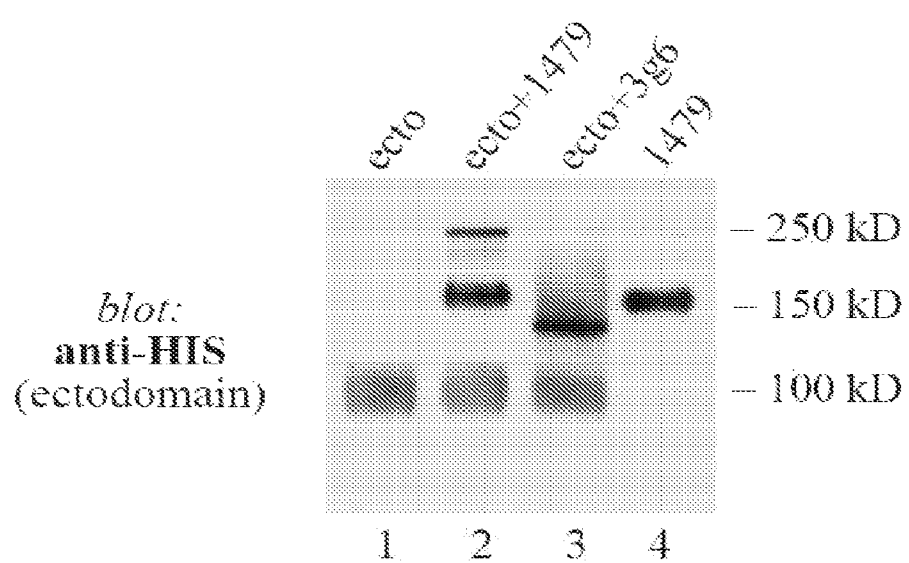
FIG. 7 shows the results of an in vitro binding assay carried out with a recombinant HER4 ectodomain and mAb 1479.

To more directly demonstrate that mAb 1479 can recognize the soluble ectodomain of HER4, an in vitro binding assay was carried out with a recombinant HER4 ectodomain and mAb 1479. When the ectodomain and the antibody were incubated together they formed a complex of 250 kDa that was detected in Western analysis (FIG. 7). In this assay, HIS-tagged recombinant HER4 ectodomain (2 g) was incubated with 0.5 ug of either mAb 1479 or the negative control antibody 3g6 for 15 min and the formation of a protein complex was visualized by western analysis under nonreducing conditions using an anti-HIS antibody. In FIG. 7, free ectodomain is seen migrating at the size of 100 kDa, free antibodies at 150 kDa and the complex formed by the ectodomain bound to the antibody at 250 kDa.

Figure 8:
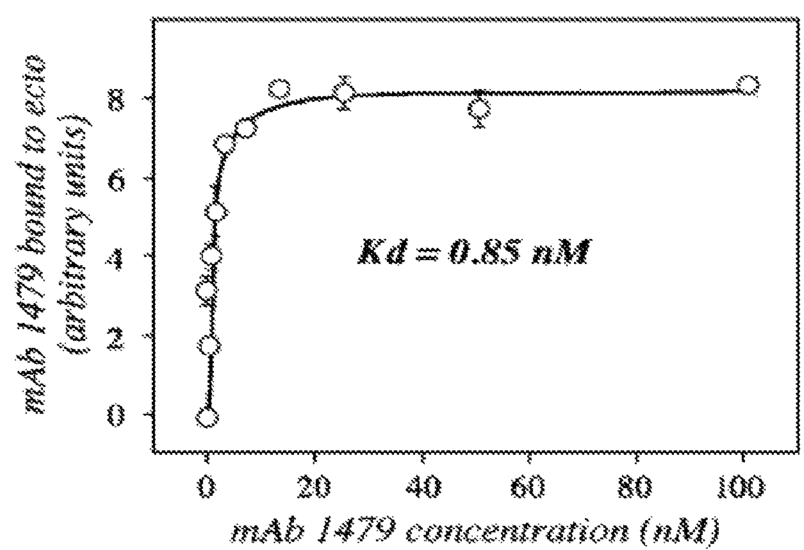
FIG. 8 is a nonlinear affinity curve of an enzyme-linked immunosorbent assay (ELISA) measuring mAb 1479 binding to recombinant HER4 ectodomain.

Neuregulin-1 alone also demonstrated binding to recombinant HER4 ectodomain, confirming that the recombinant ectodomain used for the experimentation was functional. Moreover, an ELISA with microwell-plate-immobilized HIS-tagged HER4 ectodomain (100 ng) gave a Kd value of 0.85 nM+/−0.077 for the interaction with mAb 1479 (at concentrations ranging from 0.195 to 100 nM) (FIG. 8). These observations demonstrate that mAb 1479 binds HER4 ectodomain with a relatively high affinity.

Example 4—HER4 Ectodomain Shedding is Enhanced in Breast Cancer In Vivo

Figure 9:
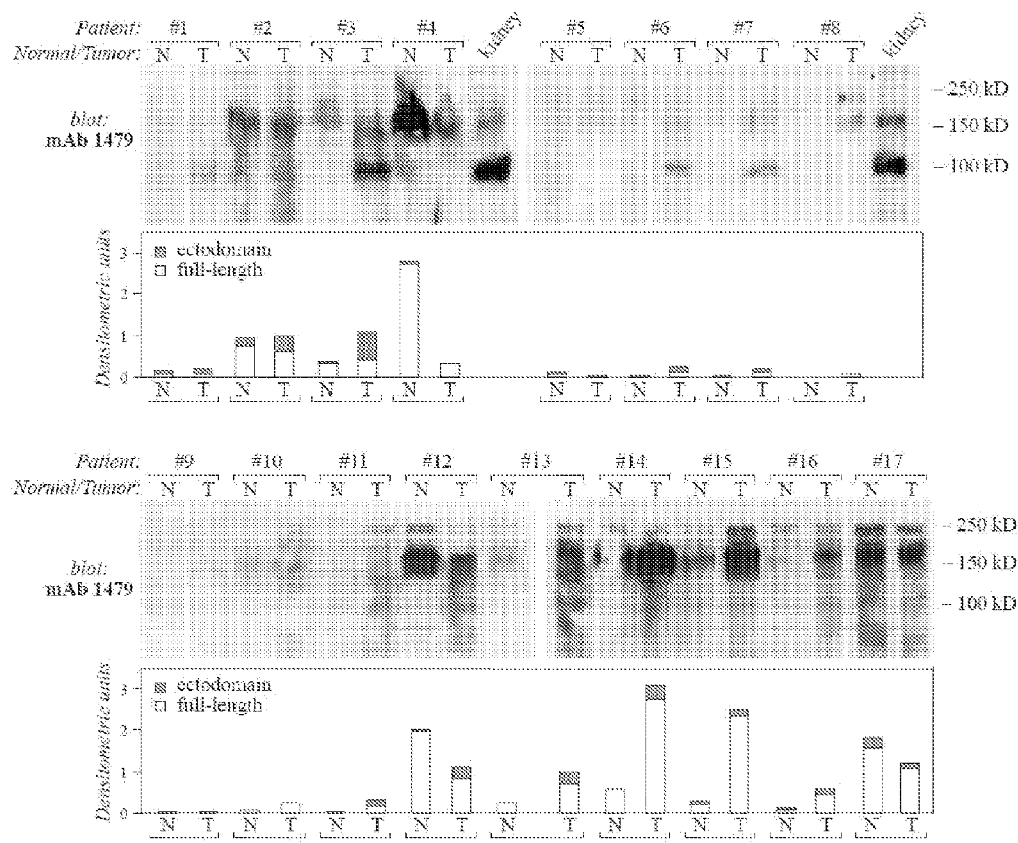
FIG. 9 is a Western blot analysis of 17 paired normal breast (N)/breast tumor (T) tissue samples using mAb 1479 to detect ectodomain shedding. Densitometric quantitation of the expression levels of 100 kDa HER4 ectodomain (gray) and 150 kDa full-length HER4 (white) are shown underneath each western lane.

Cleavable JM-a isoforms, as well as the TACE enzyme capable of cleaving HER4, are overexpressed in breast tumor tissues in vivo (29), and carboxyterminal HER4 epitope is localized to nuclei more frequently in breast cancer tissue than in histologically normal mammary epithelium (35). Moreover, nuclear localization of HER4 immunoreactivity is associated with unfavorable survival when compared to cell surface immunoreactivity (29). These findings imply that HER4 cleavage and ectodomain shedding are enhanced in breast cancer, as compared to normal breast tissue, and that the cleavage is of biological significance. To test whether transformation of histologically normal breast tissue to breast carcinoma is associated with enhanced shedding of HER4 ectodomain, 17 matched normal breast/breast cancer tissue pairs were analyzed by Western blotting with mAb 1479 (FIG. 9). The sample pairs consisted of frozen tissue material from breast cancer patients from whom both cancer tissue and histologically normal adjacent tissue were available. The Western data, generated under non-reducing conditions, were scored for the intensities of the 150 kD signal representing full-length HER4 and the 100 kD signal representing soluble ectodomain. Nine out of 17 (53%) of the tumor samples demonstrated increased total HER4 expression when compared to the matched normal tissue pair. Only one tumor sample (1/17; 6%) had no detectable HER4 expression compared as opposed to six samples of normal breast tissue (6/17; 35%) with no detectable HER4. Similar findings of enhanced HER4 protein levels in cancer versus normal tissues were also obtained by immunohistochemistry with mAb 1479 using the same sample pairs.

Figure 10:
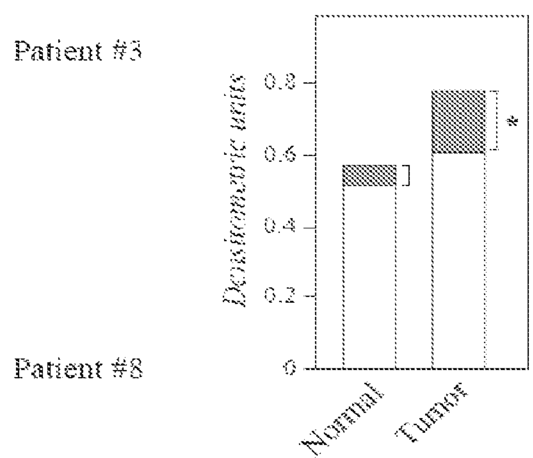
FIG. 10 is a graph showing the mean expression of HER4 ectodomain and full-length receptor in the 17 matched normal and breast tumor tissue pairs quantitated by densitometry. *, the fraction of total HER4 present as ectodomain was greater within tumor tissues, when compared to the matched normal tissue controls (gray boxes; $P<0.05$; Wilcoxon signed-rank test).

Interestingly, signal for HER4 ectodomain was observed in 12 (12/16; 75%) of HER4 positive tumor samples but only in two HER4-positive normal breast tissue samples (2/11; 18%). When the Western signals for the 150 kD full-length receptor and the 100 kD ectodomain were quantitated by densitometry the tumor tissues expressed significantly more HER4 ectodomain when compared to normal tissues (P=0.015) (FIG. 10). However, the difference in the expression of full-length HER4 did not reach statistical significance (P=0.33). The amount of detected 100 kD ectodomain also did not correlate with the total amount of HER4 (100 kD+150 kD) in the same sample (P=0.15). These data suggest that the up-regulation of the quantities of ectodomain in cancer tissue were not a simple consequence of more protein being made. Moreover, of the two patients who demonstrated similar full-length HER4 levels in normal and cancer tissues (patients #1 and #3), both demonstrated presence of soluble ectodomain only in the tumor sample. Taken together, these data indicate that shedding of HER4 ectodomain is enhanced during breast cancer progression, and that mAb 1479 can be used to detect HER4 ectodomain shed by human tumor tissue.

Example 5—mAb 1479 Suppresses HER4 Phosphorylation and Cleavage

Figure 11A:
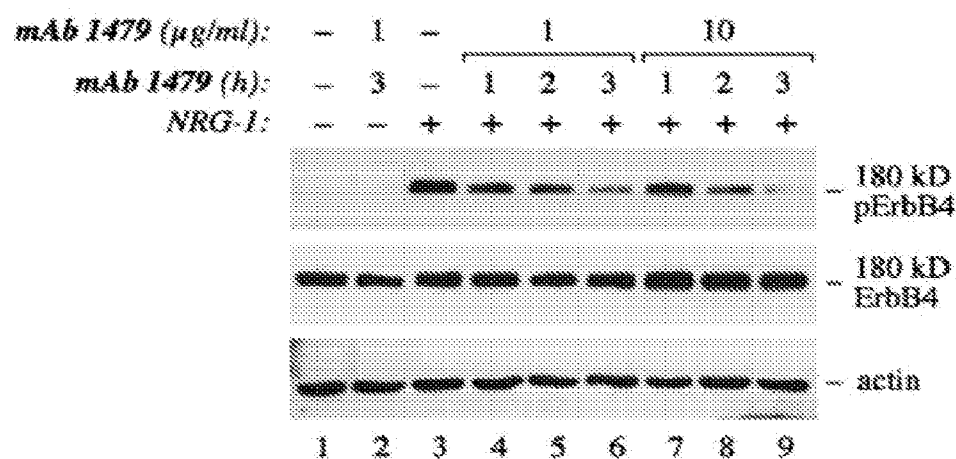
FIG. 11A is a Western blot analysis showing the effect of mAb 1479 on HER4 tyrosine phosphorylation of NRG-1 stimulated MCF-7 breast cancer cells. The membrane was reblotted with anti-HER4 (Abeam) and anti-actin as controls.

To analyze the consequences of mAb 1479 binding on HER4 function, HER4 phosphorylation was measured in MCF-7 breast cancer cells naturally expressing JM-a isoforms (26). MCF-7 cells were stimulated for 1, 2, or 3 hours with 0, 1, or 10 ug/ml mAb 1479 before a 15 minute stimulation with 50 ng/ml neuregulin-1 (NRG-1), and analyzed for HER4 tyrosine phosphorylation using a phospho-specific antibody against pTyr1284 of HER4. The membrane was reblotted with anti-HER4 (Abeam) and anti-actin. mAb 1479 significantly suppressed NRG-1-stimulated phosphorylation of HER4 (FIG. 11A).

Since activation of HER4 may also regulate HER4 cleavage (36) the effect of mAb on both basal and phorbol 13-myristate 12-acetate (PMA)-stimulated HER4 cleavage was assessed. Shedding of the 100 kDa HER4 ectodomain into the culture medium of COS-7 transfectants expressing HER4 JM-a CYT-2 was analyzed by western blotting with an anti-HER4 antibody mAb 1464 after stimulating the cells for 24 h with 1 g/ml mAb 1479 or a control antibody mAb 1475. Total cell lysates from the same experiment were analyzed by western blotting with anti-HER4 (Abeam) and anti-actin (FIG. 11B).

Figure 11B:
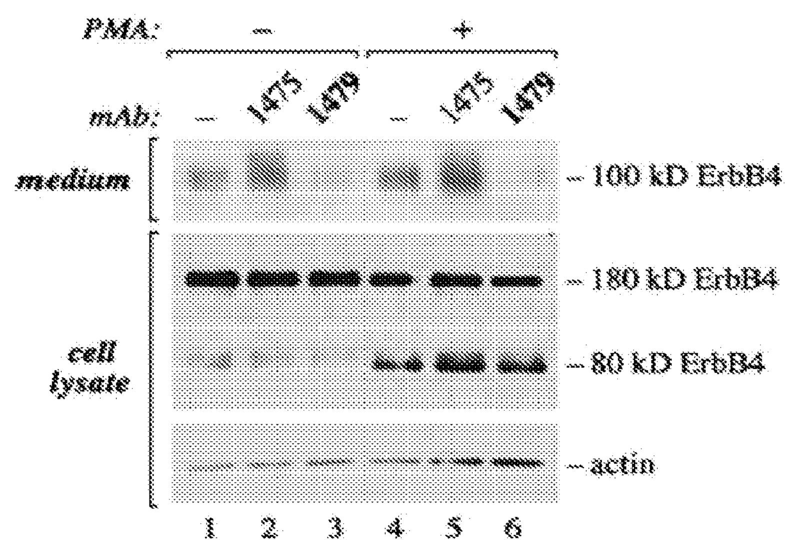
FIG. 11B is a Western blot analysis showing the effect of mAb 1479 on shedding of 100 kDa HER4 ectodomain into the culture medium of COS-7 transfectants expressing HER4 JM-a CYT-2. Total cell lysates from the same experiment were analyzed by western blotting with anti-HER4 (Abeam) and anti-actin.

Treatment with mAb 1479 significantly decreased the amount of soluble 110 kDa HER4 ectodomain shed into the medium of COS-7 transfectants, when compared to non-treated cells or cells treated with mAb1475 which recognizes a different HER4 epitope (FIG. 11B). These data indicate that mAb 1479 blocks tyrosine phosphorylation and cleavage of HER4 JM-a isoforms.

Figure 12:
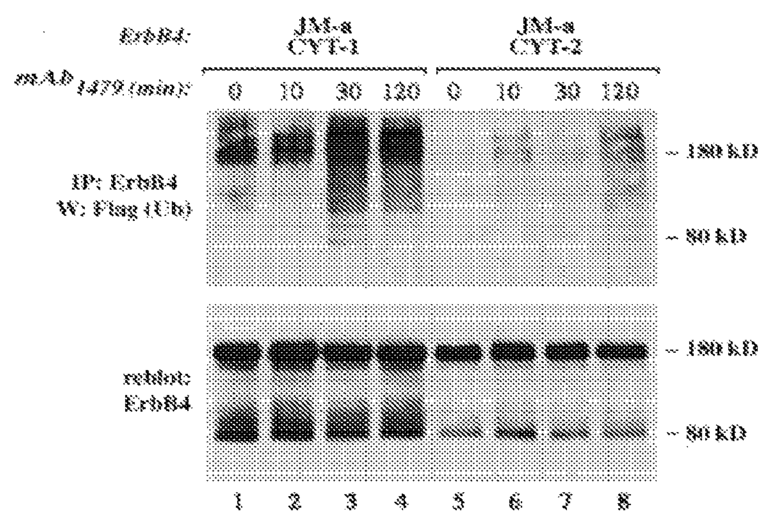
FIG. 12 is a Western blot analysis showing the effect of mAb 1479 on ubiquitination of cleavable JM-a isoforms of HER4.

Example 6—mAb 1479 is Efficiently Internalized by a Mechanism Dependent on HER4 but Independent of HER4 Kinase Activity Inhibition of tumor growth by anti-HER2 antibodies has been shown to be associated with an intrinsic ability of the mAbs to induce endocytosis (37). mAb 1479 was observed to become rapidly depleted from the culture media of cells expressing HER4 but not from media of vector control cells. To address whether this was due to HER4-mediated internalization of the mAb, COS-7 cells transiently expressing HER4 JM-a were treated with mAb 1479 and analyzed by confocal microscopy to visualize the subcellular localization of the antibody. After five minutes of incubation mAb 1479 was detected predominantly on the cell surfaces. However, in two hours the antibody had been internalized to the cytosol and partially co-localized with green fluorescent protein (GFP)-tagged Rab5, a marker of early endocytic vesicles. No cytoplasmic localization of mAb 1479 was observed in cells expressing the JM-b isoform. Although dependent on HER4 expression, internalization of mAb 1479 did not require HER4 kinase activity as mAb 1479 was efficiently internalized also when COS-7 cells transiently expressing a kinase-dead HER4 JM-a construct (K751R) were analyzed.

mAb 1479 also enhanced ubiquitination of cleavable JM-a isoforms of HER4, indicating that mAB 1479 may actively stimulate ErB4 endocytosis into degradative vesicles as shown in FIG. 12. The assay in FIG. 12 was performed using COS-7 cells transiently expressing JM-a CYT-1 or JM-a CYT-2 together with Flag-tagged ubiquitin. The cells were treated for 0, 10, 30, or 120 minutes with 2 ug/ml mAb1479 and analyzed for HER4 ubiquitination by anti-HER4 immunoprecipitation with HFR-1 followed by western blotting with an anti-Flag antibody. Loading of HER4 protein was controlled by reblotting with anti-HER4 (Abeam) antibody.

Figure 13:
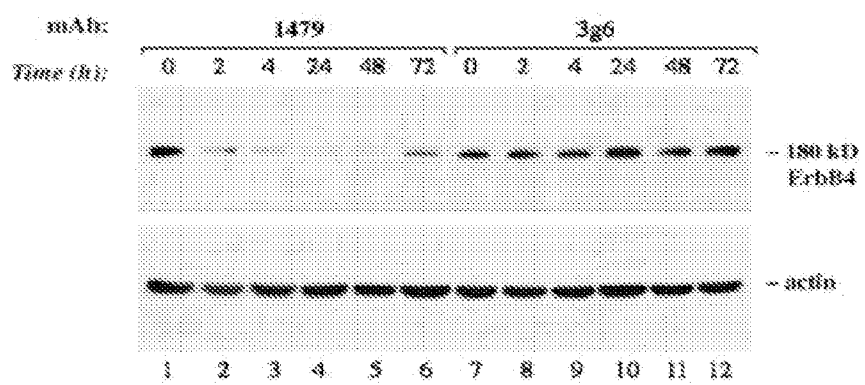
FIG. 13 is a Western blot analysis showing effect of mAb 1479 on HER4 expression levels.

Cetuximab has been suggested to suppress tumor growth by facilitating EGFR down-regulation (38). To address whether the efficient internalization of mAb 1479 into cells expressing HER4 associated with stimulation of HER4 down-regulation, MCF-7 cells expressing moderate levels of endogenous HER4 were cultured for up to 72 hours in the presence of 1 μg/ml mAb 1479 and the total levels of full-length HER4 were analyzed by Western blotting (FIG. 13). Steady-state HER4 protein expression levels were analyzed by western blotting with an anti-HER4 (Abcam) antibody and loading was controlled with anti-actin. Treatment with mAb 1479, but not with the control antibody 3g6 (1 ug/ml), significantly decreased the HER4 steady-state levels. The effect was already seen at 2 hour time point and lasted for the 72-hour duration of the experiment.

Figure 14:
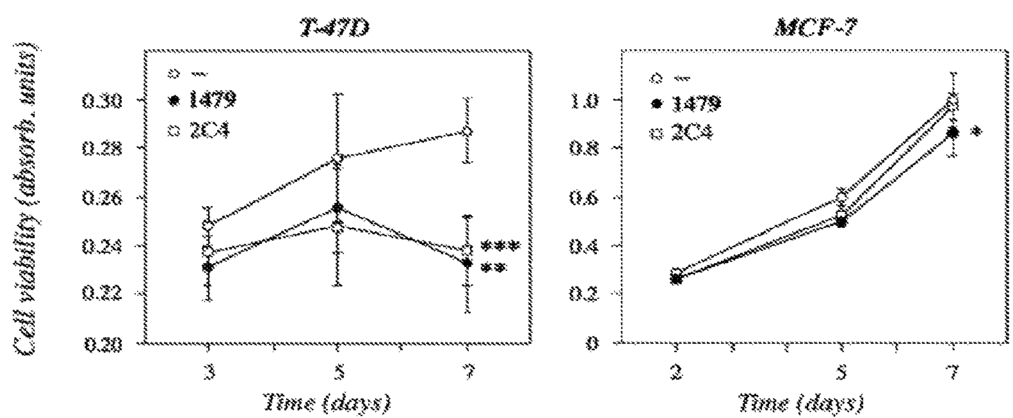
FIG. 14 is a graph showing the effect of mAb 1479 on proliferation of the human breast cancer cell lines T-47D and MCF-7 as compared to control antibody 2C4.
Figure 15:
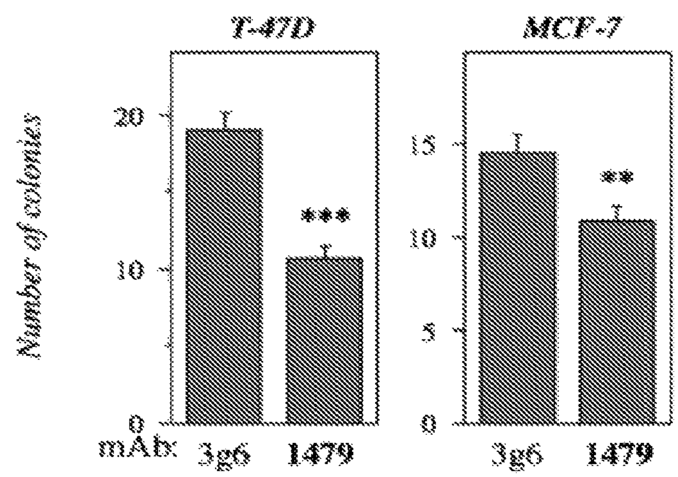
FIG. 15 is a graph showing the effect of mAb 1479 on anchorage independent growth of human breast cancer cell lines T-47D and MCF-7 as compared to control antibody 3g6 as indicated by a soft agar colony formation assay.

Example 7—mAb 1479 Suppresses Proliferation and Colony Formation of Breast Cancer Cells To study the effect of mAb 1479 on breast cancer cell growth, MTS assays measuring the amount of viable cells were carried out with human breast cancer cell lines. mAb 1479 significantly suppressed the proliferation of T-47D (P=0.0014) and MCF-7 (P=0.047) cells (FIG. 14). In this assay, the cell lines were treated with 1 ug/ml of mAb 1479 or the positive control antibody 2C4 (Genentech) for the indicated periods of time. The number of viable cells were estimated by MTS assay. The antibodies significantly reduced the number of viable cells at the 7-day time point (*P<0.05; P<0.01; *P<0.001; Student's t-test, five independent experiments carried out in triplicate). The effect seen with mAb 1479 was similar or more potent when compared to the anti-HER2 antibody 2C4 (Genentech), that blocks HER2 heterodimerization with other HER receptors (39).

mAb 1479 significantly suppressed the anchorage-independent growth of both T-47D (P<0.001) and MCF-7 (P=0.043) cells in soft agar colony formation assays (FIG. 15). Colonies over the size of 8 cells per×20 field at the 14-day time point were calculated from 10 microscopic fields per experiment carried out three times. mAb 1479 treatment significantly reduced the number of colonies at the 14-day time point when compared to the control antibody 3g6 (P<0.01; *P<0.001; Student's t-test, three independent experiments carried out in triplicate). Mean and standard deviations are shown in FIG. 15.

REFERENCES

1. Yarden Y, Sliwkowski M X. Untangling the ErbB signalling network. Nat Rev Mol Cell Biol 2001; 2(2):127-37.

2. Hynes N E, Lane H A. ERBB receptors and cancer: the complexity of targeted inhibitors. Nat Rev Cancer 2005; 5(5):341-54.
3. Mendelsohn J, Baselga J. The EGF receptor family as targets for cancer therapy. Oncogene 2000; 19(56):6550-65.
4. Slamon D J, Clark G M, Wong S G, Levin W J, Ullrich A, McGuire W L. Human breast cancer: correlation of relapse and survival with amplification of the HER-2/neu oncogene. Science 1987; 235(4785):177-82.
5. Graham J, Muhsin M, Kirkpatrick P. Cetuximab. Nat Rev Drug Discov 2004; 3(7):549-50.
6. Sarup J C, Johnson R M, King K L, et al. Characterization of an anti-p185HER2 monoclonal antibody that stimulates receptor function and inhibits tumor cell growth. Growth Regul 1991; 1(2):72-82.
7. Austin C D, De Maziere A M, Pisacane P I, et al. Endocytosis and sorting of ErbB2 and the site of action of cancer therapeutics trastuzumab and geldanamycin. Mol Biol Cell 2004; 15(12):5268-82.
8. Molina M A, Codony-Servat J, Albanell J, Rojo F, Arribas J, Baselga J. Trastuzumab (herceptin), a humanized anti-Her2 receptor monoclonal antibody, inhibits basal and activated Her2 ectodomain cleavage in breast cancer cells. Cancer Res 2001; 61(12):4744-9.
9. Clynes R A, Towers T L, Presta L G, Ravetch J V Inhibitory Fc receptors modulate in vivo cytoxicity against tumor targets. Nat Med 2000; 6(4):443-6.
10. Srinivasan R, Poulsom R, Hurst H C, Gullick W J. Expression of the c-erbB-4/HER4 protein and mRNA in normal human fetal and adult tissues and in a survey of nine solid tumour types. J Pathol 1998; 185(3):236-45.
11. Witton C J, Reeves J R, Going J J, Cooke T G, Bartlett J M. Expression of the HER1-4 family of receptor tyrosine kinases in breast cancer. J Pathol 2003; 200(3):290-7.
12. Haugen D R, Akslen L A, Varhaug J E, Lillehaug J R. Expression of c-erbB-3 and c-erbB-4 proteins in papillary thyroid carcinomas. Cancer Res 1996; 56(6):1184-8.
13. Furger C, Fiddes R J, Quinn D I, Bova R J, Daly R J, Sutherland R L. Granulosa cell tumors express HER4 and are sensitive to the cytotoxic action of heregulin-beta2/PE40. Cancer Res 1998; 58(9):1773-8.
14. Srinivasan R, Benton E, McCormick F, Thomas H, Gullick W J. Expression of the c-crbB-3/HER-3 and c-erbB-4/HER-4 growth factor receptors and their ligands, neuregulin-1 alpha, neuregulin-1 beta, and betacellulin, in normal endometrium and endometrial cancer. Clin Cancer Res 1999; 5(10):2877-83.
15. Gilbertson R J, Perry R H, Kelly P J, Pearson A D, Luncc J. Prognostic significance of HER2 and HER4 coexpression in childhood medulloblastoma. Cancer Res 1997; 57(15):3272-80.
16. Gilbertson R J, Bentley L, Hernan R, et al. ERBB receptor signaling promotes ependymoma cell proliferation and represents a potential novel therapeutic target for this disease. Clin Cancer Res 2002; 8(10):3054-64.
17. Gullick W J. c-crbB-4/HER4: friend or foe? J Pathol 2003; 200(3):279-81.
18. Junttila T T, Sundvall M, Maatta J A, Elenius K. ErbB4 and its isoforms: selective regulation of growth factor responses by naturally occurring receptor variants. Trends Cardiovasc Med 2000; 10(7):304-10.
19. Junttila T T, Laato M, Vahlberg T, et al. Identification of patients with transitional cell carcinoma of the bladder overexpressing ErbB2, ErbB3, or specific ErbB4 isoforms: real-time reverse transcription-PCR analysis in estimation of ErbB receptor status from cancer patients. Clin Cancer Res 2003; 9(14):5346-57.
20. Elenius K, Choi C J, Paul S, Santiestevan E, Nishi E, Klagsbrun M. Characterization of a naturally occurring ErbB4 isoform that does not bind or activate phosphatidyl inositol 3-kinase. Oncogene 1999; 18(16):2607-15.
21. Kainulainen V, Sundvall M, Maatta J A, Santiestevan E, Klagsbrun M, Elenius K. A natural ErbB4 isoform that does not activate phosphoinositide 3-kinase mediates proliferation but not survival or chemotaxis. J Biol Chem 2000; 275(12):8641-9.
22. Rio C, Buxbaum J D, Peschon J J, Corfas G. Tumor necrosis factor-alpha-converting enzyme is required for cleavage of erbB4/HER4. J Biol Chem 2000; 275(14):10379-87.
23. Elenius K, Corfas G, Paul S, et al. A novel juxtamembrane domain isoform of HER4/ErbB4. Isoform-specific tissue distribution and differential processing in response to phorbol ester. J Biol Chem 1997; 272(42):26761-8.
24. Lee H J, Jung K M, Huang Y Z, et al. Presenilin-dependent gamma-secretase-like intramembrane cleavage of ErbB4. J Biol Chem 2002; 277(8):6318-23.
25. Komuro A, Nagai M, Navin N E, Sudol M. W W domain-containing protein YAP associates with ErbB-4 and acts as a co-transcriptional activator for the carboxyl-terminal fragment of ErbB-4 that translocates to the nucleus. J Biol Chem 2003; 278(35):33334-41.
26. Määttä J A, Sundvall M, Junttila T T, et al. Proteolytic cleavage and phosphorylation of a tumor-associated ErbB4 isoform promote ligand-independent survival and cancer cell growth. Mol Biol Cell 2006; 17(1):67-79.
27. Ni C Y, Murphy M P, Golde T E, Carpenter G. gamma-Secretase cleavage and nuclear localization of ErbB-4 receptor tyrosine kinase. Science 2001; 294(5549):2179-81.
28. Schlessinger J, Lemmon M A. Nuclear signaling by receptor tyrosine kinases: the first robin of spring. Cell 2006; 127(1):45-8.
29. Junttila T T, Sundvall M, Lundin M, et al. Cleavable ErbB4 isoform in estrogen receptor-regulated growth of breast cancer cells. Cancer Res 2005; 65(4):1384-93.
30. Plowman G D, Culouscou J M, Whitney G S, et al. Ligand-specific activation of HER4/p180HER4, a fourth member of the epidermal growth factor receptor family. Proc Natl Acad Sci USA 1993; 90(5):1746-50.
31. Zhang K, Sun J, Liu N, et al. Transformation of NIH 3T3 cells by HER3 or HER4 receptors requires the presence of HER1 or HER2. J Biol Chem 1996; 271(7):3884-90.
32. Sundvall M, Peri L, Maatta J A, et al. Differential nuclear localization and kinase activity of alternative ErbB4 intracellular domains. Oncogene 2007.
33. Vecchi M, Baulida J, Carpenter G. Selective cleavage of the heregulin receptor ErbB-4 by protein kinase C activation. J Biol Chem 1996; 271(31):18989-95.
34. Gomes A Q, Ali B R, Ramalho J S, et al. Membrane targeting of Rab GTPases is influenced by the prenylation motif Mol Biol Cell 2003; 14(5):1882-99.
35. Srinivasan R, Gillett C E, Barnes D M, Gullick W J. Nuclear expression of the c-erbB-4/HER-4 growth factor receptor in invasive breast cancers. Cancer Res 2000; 60(6):1483-7.
36. Cheng Q C, Tikhomirov O, Zhou W, Carpenter G. Ectodomain cleavage of ErbB-4: characterization of the cleavage site and m80 fragment. J Biol Chem 2003; 278(40):38421-7.
37. Hurwitz E, Stancovski I, Sela M, Yarden Y. Suppression and promotion of tumor growth by monoclonal antibodies to ErbB-2 differentially correlate with cellular uptake. Proc Natl Acad Sci USA 1995; 92(8):3353-7.

38. Sunada H, Magun B E, Mendelsohn J, MacLeod C L. Monoclonal antibody against epidermal growth factor receptor is internalized without stimulating receptor phosphorylation. Proc Natl Acad Sci USA 1986; 83(11):3825-9.

39. Franklin M C, Carey K D, Vajdos F F, Leahy D J, de Vos A M, Sliwkowski M X. Insights into ErbB signaling from the structure of the ErbB2-pertuzumab complex. Cancer Cell 2004; 5(4):317-28.

40. Barnes N L, Khavari S, Boland G P, Cramer A, Knox W F, Bundred N J. Absence of HER4 expression predicts recurrence of ductal carcinoma in situ of the breast. Clin Cancer Res 2005; 11(6):2163-8.

41. Suo Z, Risberg B, Kalsson M G, et al. EGFR family expression in breast carcinomas. c-erbB-2 and c-erbB-4 receptors have different effects on survival. J Pathol 2002; 196(1):17-25.

42. Bieche I, Onody P, Tozlu S, Driouch K, Vidaud M, Lidereau R. Prognostic value of ERBB family mRNA expression in breast carcinomas. Int J Cancer 2003; 106(5):758-65.

43. Lodge A J, Anderson J J, Gullick W J, Haugk B, Leonard R C, Angus B. Type 1 growth factor receptor expression in node positive breast cancer: adverse prognostic significance of c-erbB-4. J Clin Pathol 2003; 56(4):300-4.

44. Muraoka-Cook R S, Sandahl M, Husted C, et al. The intracellular domain of ErbB4 induces differentiation of mammary epithelial cells. Mol Biol Cell 2006; 17(9): 4118-29.

45. Stern D F. ErbBs in mammary development. Exp Cell Res 2003; 284(1):89-98.

46. Tang C K, Concepcion X Z, Milan M, Gong X, Montgomery E, Lippman M E. Ribozyme-mediated down-regulation of ErbB-4 in estrogen receptor-positive breast cancer cells inhibits proliferation both in vitro and in vivo. Cancer Res 1999; 59(20):5315-22.

47. Zhu Y, Sullivan L L, Nair S S, et al. Coregulation of Estrogen Receptor by ErbB4/HER4 Establishes a Growth-Promoting Autocrine Signal in Breast Tumor Cells. Cancer Res 2006; 66(16):7991-8.

48. Prewett M, Rothman M, Waksal H, Feldman M, Bander N H, Hicklin D J. Mouse-human chimeric anti-epidermal growth factor receptor antibody C225 inhibits the growth of human renal cell carcinoma xenografts in nude mice. Clin Cancer Res 1998; 4(12):2957-66.

49. Agus D B, Akita R W, Fox W D, et al. Targeting ligand-activated ErbB2 signaling inhibits breast and prostate tumor growth. Cancer Cell 2002; 2(2):127-37.

50. Cho H S, Mason K, Ramyar K X, et al. Structure of the extracellular region of HER2 alone and in complex with the Herceptin Fab. Nature 2003; 421(6924):756-60.

51. Baulida J, Kraus M H, Alimandi M, Di Fiore P P, Carpenter G. All ErbB receptors other than the epidermal growth factor receptor are endocytosis impaired. J Biol Chem 1996; 271(9):5251-7.

52. Liu Y, Tao Y M, Woo R S, Xiong W C, Mei L. Stimulated ErbB4 internalization is necessary for neuregulin signaling in neurons. Biochem Biophys Res Commun 2007; 354(2):505-10.

53. Cuello M, Ettenberg S A, Clark A S, et al. Down-regulation of the erbB-2 receptor by trastuzumab (herceptin) enhances tumor necrosis factor-related apoptosis-inducing ligand-mediated apoptosis in breast and ovarian cancer cell lines that overexpress erbB-2. Cancer Res 2001; 61(12):4892-900.

54. Klapper L N, Waterman H, Sela M, Yarden Y. Tumor-inhibitory antibodies to HER-2/ErbB-2 may act by recruiting c-Cbl and enhancing ubiquitination of HER-2. Cancer Res 2000; 60(13):3384-8.

55. Carter P. Improving the efficacy of antibody-based cancer therapies. Nat Rev Cancer 2001; 1(2):118-29.

56. Gilmore J L, Riese D J, 2nd. secErbB4-26/549 antagonizes ligand-induced HER4 tyrosine phosphorylation. Oncol Res 2004; 14(11-12):589-602.

57. Bao J, Wolpowitz D, Role L W, Talmage D A. Back signaling by the Nrg-1 intracellular domain. J Cell Biol 2003; 161(6):1133-41.

58. Iivanainen E, Paatero I, Heikkinen S M, et al. Intra- and extracellular signaling by endothelial neuregulin-1. Exp Cell Res 2007.

59. Borrell-Pages M, Rojo F, Albanell J, Baselga 5, Arribas J. TACE is required for the activation of the EGFR by TGF-alpha in tumors. Embo J 2003; 22(5):1114-24.

60. Gilmour L M, Macleod K G, McCaig A, Gullick W J, Smyth J F, Langdon S P. Expression of erbB-4/HER-4 growth factor receptor isoforms in ovarian cancer. Cancer Res 2001; 61(5):2169-76.

61. Paborsky L R, et al., Mammalian Cell Transient Expression of Tissue Factor for Production of Antigen. Protein Eng. 1990; 3(6):547-53.

62. Chu, T. F., et al., Cardiotoxicity associated with tyrosine kinase inhibitor sunitinib. Lancet 2007; 370 (9604):2011-2019.

63. Force, T. and Kerkela, R., Cardiotoxicity of the new cancer therapeutics—mechanisms of, and approaches to, the problem. Drug Discov Today 2008:13(17-18):778-784.

64. Yeh, E. T. H., and Bickford, C. L., Cardiovascular Complications of Cancer Therapy. J. Am. Coll. Cardio. 2009:53(24): 2231-2247.

65. Ding, L., et al, Somatic Mutations affect key pathways in lung adenocarcinoma. Nature 2008:455:1069-1075.

66. Prickett, T. D., et al., Analysis of the tyrosine kinome in melanoma reveals recurrent mutations in ERBB4. Nature Genetics 2009:41:1127-1132 (2009).

We claim:

1. An isolated anti-HER4 antibody, or humanized form thereof, produced by the hybridoma cell line deposited with the ATCC having accession No. PTA-9655.

2. The antibody of claim 1, wherein the antibody is linked to a cytotoxic agent.

3. The antibody of claim 1, wherein the antibody reduces HER4 ectodomain shedding.

* * * * *

SEQUENCE LISTING

```
<160> NUMBER OF SEQ ID NOS: 4

<210> SEQ ID NO 1
<211> LENGTH: 23
<212> TYPE: PRT
<213> ORGANISM: Homo Sapiens

<400> SEQUENCE: 1

Asn Gly Pro Thr Ser His Asp Cys Ile Tyr Tyr Pro Trp Thr Gly His
```

-continued

```
1               5                   10                  15

Ser Thr Leu Pro Gln His Ala
            20


<210> SEQ ID NO 2
<211> LENGTH: 13
<212> TYPE: PRT
<213> ORGANISM: Homo Sapiens

<400> SEQUENCE: 2

Ile Gly Ser Ser Ile Glu Asp Cys Ile Gly Leu Met Asp
1               5                   10


<210> SEQ ID NO 3
<211> LENGTH: 32
<212> TYPE: DNA
<213> ORGANISM: Artificial Sequence
<220> FEATURE:
<223> OTHER INFORMATION: PCR PRIMER

<400> SEQUENCE: 3

ttggtaccgc accatgaagc cggcgacagg ac                                 32


<210> SEQ ID NO 4
<211> LENGTH: 49
<212> TYPE: DNA
<213> ORGANISM: Artificial Sequence
<220> FEATURE:
<223> OTHER INFORMATION: PCR PRIMER

<400> SEQUENCE: 4

ttatctcgag ttagtgatgg tgatggtgat gttgtggtaa agtggaatg                49
```